US012303553B2

(12) United States Patent
Sprogøe

(10) Patent No.: US 12,303,553 B2
(45) Date of Patent: May 20, 2025

(54) LONG-ACTING GROWTH HORMONE DOSAGE FORMS WITH SUPERIOR EFFICACY TO DAILY SOMATROPIN

(71) Applicant: Ascendis Pharma Endocrinology Division A/S, Hellerup (DK)

(72) Inventor: Kennett Sprogøe, Hellerup (DK)

(73) Assignee: ASCENDIS PHARMA ENDOCRINOLOGY DIVISION A/S, Hellerup (DK)

( * ) Notice: Subject to any disclaimer, the term of this patent is extended or adjusted under 35 U.S.C. 154(b) by 303 days.

(21) Appl. No.: 17/310,993

(22) PCT Filed: Mar. 3, 2020

(86) PCT No.: PCT/EP2020/055513
§ 371 (c)(1),
(2) Date: Sep. 3, 2021

(87) PCT Pub. No.: WO2020/178273
PCT Pub. Date: Sep. 10, 2020

(65) Prior Publication Data
US 2022/0088147 A1    Mar. 24, 2022

(30) Foreign Application Priority Data
Mar. 4, 2019  (EP) .................... 19160459

(51) Int. Cl.
*A61K 38/27* (2006.01)
*A61K 9/00* (2006.01)
*A61K 9/19* (2006.01)
*A61P 5/06* (2006.01)

(52) U.S. Cl.
CPC .............. *A61K 38/27* (2013.01); *A61P 5/06* (2018.01)

(58) Field of Classification Search
CPC ........ A61K 38/27; A61K 9/0024; A61K 9/19; A61K 9/00; A61P 5/06
See application file for complete search history.

(56) References Cited

U.S. PATENT DOCUMENTS

| 4,179,337 | A | 12/1979 | Davis et al. |
| 5,057,417 | A | 10/1991 | Hammonds et al. |
| 5,073,627 | A | 12/1991 | Curtis et al. |
| 5,171,220 | A | 12/1992 | Morimoto |
| 5,179,080 | A | 1/1993 | Rothkopf et al. |
| 5,472,706 | A | 12/1995 | Friedman et al. |
| 5,478,925 | A | 12/1995 | Wallach et al. |
| 5,645,010 | A | 7/1997 | Lundstrom |
| 5,971,953 | A | 10/1999 | Bachynsky |
| 6,284,282 | B1 | 9/2001 | Maa et al. |
| 7,144,978 | B2 | 12/2006 | Huang et al. |
| 7,879,588 | B2 | 2/2011 | Vetter et al. |
| 7,968,085 | B2 | 6/2011 | Hersel et al. |
| 9,272,048 | B2 | 3/2016 | Rau et al. |
| 9,511,122 | B2 | 12/2016 | Rau et al. |
| 9,919,033 | B2 | 3/2018 | Rau et al. |
| 10,098,930 | B2 | 10/2018 | Rau et al. |
| 10,682,395 | B2 | 6/2020 | Rau et al. |
| 10,799,563 | B2 | 10/2020 | Rau et al. |
| 10,960,053 | B2 | 3/2021 | Rau et al. |
| 2003/0171285 | A1 | 9/2003 | Finn et al. |
| 2006/0135427 | A1 | 6/2006 | Hays et al. |
| 2006/0183198 | A1 | 8/2006 | Buechler et al. |
| 2006/0257479 | A1 | 11/2006 | Jensen et al. |
| 2006/0275252 | A1 | 12/2006 | Harris et al. |
| 2008/0063727 | A1 | 3/2008 | Kim et al. |
| 2008/0113914 | A1 | 5/2008 | Hays et al. |
| 2008/0241102 | A1 | 10/2008 | Hersel et al. |
| 2010/0197573 | A1 | 8/2010 | Dorwald et al. |
| 2010/0291021 | A1 | 11/2010 | Vetter et al. |
| 2011/0009315 | A1 | 1/2011 | Hersel et al. |
| 2011/0053848 | A1 | 3/2011 | Cleemann et al. |
| 2011/0112021 | A1 | 5/2011 | Rau et al. |
| 2011/0172390 | A1 | 7/2011 | Vetter et al. |
| 2011/0223230 | A1 | 9/2011 | Hersel et al. |
| 2012/0035101 | A1 | 2/2012 | Fares et al. |
| 2012/0058084 | A1 | 3/2012 | Rau et al. |
| 2012/0156259 | A1 | 6/2012 | Rau et al. |
| 2012/0156260 | A1 | 6/2012 | Rau et al. |
| 2012/0322721 | A1 | 12/2012 | Rasmussen et al. |
| 2017/0312342 | A1 | 11/2017 | Sprogoe et al. |
| 2020/0261544 | A1 | 8/2020 | Rau et al. |
| 2020/0390864 | A1 | 12/2020 | Rau et al. |

(Continued)

FOREIGN PATENT DOCUMENTS

| EP | 0 211 257 | 2/1987 |
| EP | 0 022 242 | 11/1992 |
| EP | 0 809 996 | 12/1997 |

(Continued)

OTHER PUBLICATIONS

Cleland et al., "A Novel Long-Acting Human Growth Hormone Fusion Protein (VRS-317): Enhanced In Vivo Potency and Half-Life," Journal of Pharmaceutical Sciences, 2012, 101(8): 2744-2754. (Year: 2012).*
Pipelinereview, "Handok-Genexine Long-Acting hGH Therapeutic "GX-H9" Receives Approval for Phase I Trial in Europe," https://pipelinereview.com/index.php/2013082051798/Proteins-and-Peptides/Handok-Genexine, pp. 1-2, Aug. 20, 2013. (Year: 2013).*
Cleveland Clinic, "Growth Hormone Deficiency," https://my.clevelandclinic.org/health/diseases/23343-growth-hormone-deficiency-ghd, pp. 1-17, accessed Sep. 21, 2023. (Year: 2023).*
Bowie, et al., "Deciphering the message in protein sequences: tolerance to amino acid substitutions," Science. 1990; 247(4948):1306-10.

(Continued)

*Primary Examiner* — Julie Ha
(74) *Attorney, Agent, or Firm* — Alston & Bird LLP

(57) ABSTRACT

A long-acting growth hormone or a pharmaceutical formulation comprising such long-acting growth hormone for use in a method of treating growth hormone deficiency with improved outcomes is described.

12 Claims, No Drawings
Specification includes a Sequence Listing.

(56) References Cited

U.S. PATENT DOCUMENTS

2021/0220442 A1 7/2021 Rau et al.

FOREIGN PATENT DOCUMENTS

| | | |
|---|---|---|
| EP | 0 975 369 | 12/2003 |
| EP | 1 196 443 | 5/2004 |
| EP | 1 579 873 | 9/2005 |
| EP | 1 625 855 | 2/2006 |
| EP | 1 562 634 | 8/2006 |
| EP | 1 715 887 | 6/2007 |
| EP | 2 113 256 | 11/2009 |
| EP | 2 119 726 | 11/2009 |
| JP | H-1067800 | 3/1998 |
| JP | 2007-515463 | 6/2007 |
| JP | 2007-530485 A | 11/2007 |
| RU | 2229288 C2 | 5/2004 |
| WO | WO 1994/10308 | 5/1994 |
| WO | WO 1999/30727 | 6/1999 |
| WO | WO 2001/047562 | 7/2001 |
| WO | WO 2001/78683 | 10/2001 |
| WO | WO 2002-055532 A2 | 7/2002 |
| WO | WO 2002/083180 | 10/2002 |
| WO | WO 2002/089789 | 11/2002 |
| WO | WO 2003/044056 | 11/2003 |
| WO | WO 2004/043493 | 5/2004 |
| WO | WO-2005027978 A2 | 3/2005 |
| WO | WO 2005/034909 | 4/2005 |
| WO | WO 2005/061005 | 7/2005 |
| WO | WO 2006/084888 | 8/2005 |
| WO | WO 2005/079838 | 9/2005 |
| WO | WO-2005099768 A2 | 10/2005 |
| WO | WO 2006/0003014 | 1/2006 |
| WO | WO 2006/071840 | 7/2006 |
| WO | WO 2006/076471 | 7/2006 |
| WO | WO 2006/102659 | 9/2006 |
| WO | WO 2006/136586 | 12/2006 |
| WO | WO 2007/025988 | 3/2007 |
| WO | WO 2007/075534 A2 | 7/2007 |
| WO | WO 2007/114881 | 10/2007 |
| WO | WO 2008/112155 | 9/2008 |
| WO | WO-2008155134 A1 | 12/2008 |
| WO | WO 2009/095479 | 8/2009 |
| WO | WO-2009133137 A2 | 11/2009 |
| WO | WO 2011/073234 | 6/2011 |
| WO | WO 2011/073234 A2 | 6/2011 |
| WO | WO-2011123813 A2 | 10/2011 |
| WO | WO-2011144756 A1 | 11/2011 |
| WO | WO-2014060512 A1 | 4/2014 |
| WO | WO-2016079114 A1 | 5/2016 |
| WO | WO-2016079302 A1 | 5/2016 |
| WO | WO-2016109823 A1 | 7/2016 |
| WO | WO-2017136583 A1 * | 8/2017 ............. G06F 19/00 |
| WO | WO 2020/178273 A1 | 9/2020 |
| WO | WO 2022/2077798 A1 | 10/2022 |
| WO | WO 2004/019993 | 6/2023 |
| WO | WO 2008/084237 | 6/2023 |

OTHER PUBLICATIONS

Kemp et al., "Pharmacokinetic and pharmacodynamic characteristics of a long-acting growth hormone (GH) preparation (nutropin depot) in GH-deficient children," J Clin Endocrinol Metab. 2004; 89(7):3234-40.

Reiter et al., "A multicenter study of the efficacy and safety of sustained release GH in the treatment of naive pediatric patients with GH deficiency," J Clin Endocrinol Metab. 2001; 86(10):4700-6.

A. Semlaty et al., Properties and Formulation of Oral Drug Delivery Systems of Protein and Peptides, 69(6) IND1'N J. Pharmaceutical Sci. 741-747 (2007).

Adis Insight, Drug Profile, Lonapegsomatropin, Ascendis Pharma, https://adisinsight.springer.com/print/drugs/800031668, updated (Jan. 22, 2021).

Alam et al., "Synthesis and purification of a deleted human growth hormone, hGHA135-146: sensitivity to plasmin cleavage and in vitro and in vivo bioactivities", J. of Biotechnology, 78, 49-59, 2000, Elsevier.

Antezak et al., "A New Acivicin Prodrug Designed for Tumor-Targeted Delivery", Bioorganic & Medicinal Chemistry, 9, 2843-2848, 2001, Elsevier.

Barbour et al., "Population Pharmacokinetic Modeling and Simulation of Amprenavir Following Forsamprenavir/Ritonavir Administration for Dose Optimization in HIV Infected Pediatric Patients," Pediatric Pharmacol. 54(2): 206-214, (2013).

Belikov, "Farmazevtit'cheskaya Khimia (Pharmaceutical chemistry)", Part I, Moscov "Vysshaya shkola", pp. 43-45 (1993). English translation.

Buyukgebiz et al., "Localized Lipoatrophy due to Recombinant Growth Hormone Therapy in a Child with 6.7 Kilobase Gene Deletion Isolated Growth Hormone Deficiency", J. of Pediatric Endocrinology & Metabolism, 12, 95-97, 1999, Freund Publishing House Ltd., London.

Cheng et al., "Synthesis of Linear, fl-Cyclodextrin-Based Polymers and Their Camptothecin Conjugates", Bioconjugate Chem., 14, 1007-1017, 2003, American Chemical Society.

Clark et al., "Long-acting Growth Hormones Produced by Conjugation with Polyethylene Glycol", J. Biol. Chem., 271:36, 21969-21977, Sep. 1996, American Society for Biochemistry and Molecular Biology, Inc.

Cleland et al., "A Novel Long-Acting Human Growth Hormone Fusion Protein (VRS-317): Enhanced In Vivo Potency and Half-Life," Journal of Pharmaceutical Sciences, vol. 101, No. 8, pp. 2744-2754, (Aug. 2012).

Dag, et al., "Preparation of 3-Arm Star Polymers (A3) Via Diels-Alder Click Reaction," Journal of Polymer Science: Part A: Polymer Chemistry, 46, 302-313, (2007).

Davis, et al., "The effect of bovine somatotroin in a sustained release preparation (Somidobove) on milk production of cows at pasture in New Zealand," New Zealand Journal of Agricultural Research, vol. 42, 315-323, (1999).

Garman et al., "The preparation and properties of novel reversible polymer-protein conjugates", FEBS Letters, 223:2, 361-365, Nov. 1987, Elsevier.

Genentech Inc., Nutropin AQ0, obtained from http://www.accessdata.fda.gov/drugsatfda docs/labe1/2005/020522s021,0221bl.pdf, p. 1-27 (2004).

Genotropin insert, Pharmacia & Upjohn Co. LAB-0222-9.0, 2006.

Gohil, "Long-Acting Therapies Will Expand Growth Hormone Deficiency Market," Pipeline Plus vol. 40(11): 772-773, 2015.

Graham, et al., "AAS, Growth Hormone, and Insulin Abuse: Psychological and Neuroendocrine Effects," 4(3) Therapeutics and Clinical Risk Management 587-597 (2008).

Greenwald et al., "A New Aliphatic Amino Prodrug System for the Delivery of Small Molecules and Proteins Utilizing Novel PEG Derivatives," 47 J. Med. Chemistry 726-734 (2004).

Greenwald et al., "Drug Delivery Systems Based on Trimethyl Lock Lactonization: Poly(ethylene glycol) Prodrugs of Amino-Containing Compounds," 43 J. Med. Chemistry 475-487 (2000).

Greenwald et al., "Drug Delivery Systems Employing 1,4- or 1,6-Elimination: Poly (ethylene glycol) Prodrugs of Amine-Containing Compounds", J. Med. Chem., 42, 3657-3667, 1999, American Chemical Society.

Grigorian et al., "Extraordinarily stable disulfide-linked homodimer of human growth hormone", Protein Sci., 14, 902-913, Mar. 1, 2005, Cold Spring Harbor Laboratory Press.

Haffner et al., "Metabolic Clearance of Recombinant Human Growth Hormone in Health and Chronic Renal Failure", J. Clin. Invest,, 93, 1163-1171, Mar. 1994, American Society for Clinical Investigation, Inc.

Hoybye, et al., "A Phase 2, Multiple-Dose, Open-Label, Parallel-Group, Active Controlled, Safety, Tolerability, Pharmacokinetic and Pharmacodynamic Study of ACP-001 in Adult Patients with Growth Hormone Deficiency (AGHD) : What's New in Diagnosis & Treatment of GH Dysfunction? (Clinical)", The Endocrine Soci-

(56) References Cited

OTHER PUBLICATIONS ety's 94th Annual Meeting and Expo, Jun. 23-26, 2012—Houston, TX—, (Jun. 23, 2012), pp. OR29-4, XP055246166 [Y] 3,4,38,39, abstract only.

Kalia et al., "Hydrolytic Stability of Hydrazones and aames," 47 Angewandte Creme Int'l Edition 7523-7526 (2008).

Kidder et al., "Effects of Growth Hormone and Low Dose Estrogen on Bone Growth and Turnover in Long Bones of Hypophysectomized Rats," 61 Calcified Tissue Int'l 327-335 (1997).

Kumar et al., "Effect of Trehalose on Protein Structure," 18 Protein Sc. 24-36 (2009).

Lee et al., "Drug Delivery Systems Employing 1,6-Elimination: Releasable Poly(ethylene glycol) Conjugates of Proteins", Bioconjugate Chan, 12, 163-169, 2001, American Chemical Society.

Lee et al., "Targeted Enzyme-responsive Drug Carriers: Studies on the Delivery of a Combination of Drugs", Angew. Chem., 116, 1707-1710, 2004, Wiley-VCR.

Luo et al., "A Hyaluronic Acid-Taxol Antitumor Bioconjugate Targeted to Cancer Cells", Biomacromolecules, I, 208-218, 2000, American Chemical Society.

MacGillivray, et al., "Current Dosing of Growth Hormone in Children with Growth Hormone Deficiency: How Physiologic?," Pediatrics, 102: 527-530, (1998).

Machlin, L,J., "Effect of Porcine Growth Hormone on Growth and Carcass Composition of the Pig", J. of Animal Science, 35, 794-800, 1972, ASAS.

Mehta, et al., "The Use of Somatropin (Recombinant Growth Hormone) in Children of Short Stature," Pediatr Drugs, 4(1): 37-47, (2002).

Monfardini et al., "A Branched Monotnethoxypoly (Ethylene Glycol) for Protein Modification," 6 Bioconjugate Chemistry p. 62-69 (1995).

Neutropin Depot, "2.B Clean Packge Insert," FDA.gov, XP055185385, (Dec. 1999).

Nishiguchi, "What is PEG-IFN?" Strategy of New Interferon Therapy, Mebio (2002) pp. 20-23 (w/English Translation).

Nutropin Depot, Clean package insert (1999).

Palchuk et al., Weight-based Pediatric Prescribing in Ambulatory Setting, AMIA 2006, SymposiumProceedings p. 1055.

Pasut et al., "A New PEG-fl-Alanine Active Derivative for Releasable Protein Conjugation", Bioconjugate Chem., 19, 2427-2431, 2008, American Chemical Society.

Peleg-Shulman et al., "Reversible PEGylation: A Novel Technology to Release Native Interferon a2 over a Prolonged Time Period", J. Med. (hem., 47, 4897-4904, 2004, American Chemical Society.

Pfizer, Highlights of Prescribing Information, obtained from http://www.accessdataida.gov/scripts/cder/drugsatfda/index.cfm, p. 1-24 (2008).

Ranke, et al., "Derivation and Validation of a Mathematical Model for Predicting the Response to Exogenous Recombinant Human Growth Hormone (GH) in Prepubertal Children with Idiopathic GH Deficiency," The Journal of Clinical Endocrinology & Metaboliam, vol. 84, No. 4, 1174-1183, (1999).

Ron et al., "Expression of Biologically Active Recombinant Keratinocyte Growth Factor", J. of Biological Chemistry, 268:4, 2984-2988, 1993, NTH, Bethesda, Maryland.

Said et al., "Comparison on Efficacy and Safety of Three Inpatient Insulin Regimens for Management of Non-Critical Patients with Type 2 Diabetes," Pharmacol. & Pharmacy, 4: 556-565, (2013).

Sengupta et al., "An audit of primary surgical treatment for women with ovarian cancer referred to a cancer centre", British J. of Cancer, 80:3/4, 444-447, 1999, Cancer Research Campaign.

Shabat et al., "Chemical Adaptor Systems", Chem. Eur. J., 10, 2626-2634, 2004, Wiley-VCH.

Shechter et al., "New Technologies to Prolong Life-time of Peptide and Protein Drugs In vivo", International Journal of Peptide Research and Therapeutics, 13:1-2, 105-117, Jun. 2007, Springer Science+ Business Media, Inc.

Shechter et al., "Reversible PEGylation of peptide YY3-36 prolongs its inhibition of food intake in mice", FEBS Letters, 579, 2439-2444, 2005, Elsevier B.V.

SKYTROFAtm, Highlights of Prescribing Information, Reference ID: 4846899, revised (Aug. 2021).

Swanson, "How to Dose Acetaminophen or Ibuprofen," Seattle Mama Doc. 2011.

Testa. Chapter 8 of Hydrolysis in Drug and Prodrug Metabolism, 419-523, Aug. 1, 2003, John Wiley & Sons. Clinical Focus: 45th Annual Meeting of the ESPE, Hormone Red 2006, 65 (suppl 4) 29-34. Clinical Focus: 45th Annual Meeting of the ESPE, Hormone Red 2006, 65 (suppl 4) 115-154.

Thorner, et al., "Growth Hormone GH Receptor Blaockade with a PEG-Modified GH (B2036-PEG) lowers Serum Insulin-Like Growth Factro—I but Does Not Acutely Stimulate Serum GH," The Journal of Cinical Endocrinology & Metabolism, Jun. 1999; 84-6, 2098-2103.

Tsubery et al., "Prolonging the Action of Protein and Peptide Drugs by a Novel Approach of Reversible Polyethylene Glycol Modification", J. of Biological Chemistry, 279:37, 38118-38124, Sep. 2004, American Society for Biochemistry and Molecular Biology, Inc.

Veronese, "Enzymes for human therapy: surface structure modifications", Chimicaoggi, 53-56, Jan.-Feb. 1989.

Veronese, Peptide and protein PEGylation: a review of problems and solutions,: Biomaterials, 22, 405-417, (2001).

Wang, "Lyophilixation and Development of Solid Protein Pharmaceuticals," 203 Int'l J. Pharmaceutics 1-60 (2002).

Wolf et al., "Growth Hormone and Insulin Reverse Net Whole Body and Skeletal Muscle Protein Catabolismin Cancer Patients," 216(3) Annals Surgery 280-288 (1992).

Zalipsky et al., "Thiolytically Cleavable Dithiobenzyl Urethane-Linked Polymer-Protein Conjugates as Macromolecular Prodrugs: Reversible PEGylation of Proteins", Bioconjugate Chan., 18, 1869-1878, 2007, American Chemical Society.

English Translation of International Russian Office Action issued in corresponding International Application No. 2017121203 dated Oct. 15, 2019.

English Translation of Official Action issued Mar. 4, 2014 in counterpart Japanese Patent Application No. 2011-506705.

EP 21201573 European Search Report mailed Mar. 16, 2022.

PCT/EP2015/077229 International Search Report dated Feb. 6, 2016.

U.S. Appl. No. 13/515,621, Advisory Action mailed Dec. 29, 2014.
U.S. Appl. No. 13/515,621, Final Office Action mailed Sep. 23, 2015.
U.S. Appl. No. 13/515,621, Final Office Action mailed Oct. 7, 2014.
U.S. Appl. No. 13/515,621, Non-Final Office Action mailed Jan. 20, 2016.
U.S. Appl. No. 13/515,621, Non-Final Office Action mailed Apr. 14, 2015.
U.S. Appl. No. 13/515,621, Non-Final Office Action mailed Apr. 25, 2013.
U.S. Appl. No. 13/515,621, Requirement for Restriction/Election mailed Jan. 2, 2013.
U.S. Appl. No. 15/340,595, Notice of Allowance mailed Nov. 1, 2017.
U.S. Appl. No. 15/528,350, Final Office Action mailed Jan. 6, 2022.
U.S. Appl. No. 15/528,350, Non-Final Office Action mailed Nov. 20, 2022.
U.S. Appl. No. 15/901,350, Final Office Action mailed Oct. 31, 2019.
U.S. Appl. No. 15/901,350, Non-Final Office Action mailed Apr. 16, 2019.
U.S. Appl. No. 15/901,350, Notice of Allowance mailed Feb. 7, 2020.
U.S. Appl. No. 16/515,621, Notice of Allowance mailed Aug. 2, 2016.
U.S. Appl. No. 16/866,764, Final Office Action mailed Oct. 12, 2022.
U.S. Appl. No. 16/866,764, Non-Final Office Action mailed Mar. 2, 2023.

(56) References Cited

OTHER PUBLICATIONS

U.S. Appl. No. 17/006,589, Non-Final Office Action mailed Jan. 24, 2023.
U.S. Appl. No. 17/006,589, Requirement for Restriction/Election mailed Nov. 9, 2022.
U.S. Appl. No. 17/215,991, Non-Final Office Action mailed May 8, 2023.
U.S. Appl. No. 17/215,991, Requirement for Restriction/Election mailed Jan. 27, 2023.
U.S. Appl. No. 15/528,350, Final Office Action mailed Apr. 27, 2023.
WIPO Application No. PCT/EP2020/055513, PCT International Search Report mailed May 13, 2020.
WIPO Application No. PCT/2010/069710, PCT Written Opinion of the International Searching Authority mailed Feb. 28, 2012.
WIPO Application No. PCT/EP2009/055194, PCT International Preliminary Report on Patentability mailed Nov. 2, 2010.
WIPO Application No. PCT/EP2009/055194, PCT International Search Report mailed Nov. 9, 2009.
WIPO Application No. PCT/EP2010/069710, PCT International Preliminary Report on Patentability mailed Jul. 3, 2012.
WIPO Application No. PCT/EP2010/069710, PCT International Search Report mailed Feb. 28, 2012.
WIPO Application No. PCT/EP2015/076813, PCT International Search Report mailed Apr. 18, 2016.
WIPO Application No. PCT/EP2015/076913, PCT International Preliminary Report on Patentability mailed May 23, 2017.
WIPO Application No. PCT/EP2015/077229, PCT International Preliminary Report on Patentability mailed May 23, 2017.
WIPO Application No. PCT/EP2015/077229, PCT International Search Report mailed Feb. 11, 2016.
U.S. Appl. No. 16/866,764, Final Office Action mailed Aug. 2, 2023.
U.S. Appl. No. 17/215,991, Notice of Allowance and Interview Summary mailed Nov. 9, 2023.
U.S. Appl. No. 17/006,589, Notice of Allowance mailed Jul. 17, 2023.
Chatelain et al., "A Randomized Phase 2 Study of Long-Acting TransCon GH vs Daily GH in Childhood GH Deficiency," J Clin Endocrinal Metab, 102(5):1673-1682, (May 2017).
History of Changes for Study: NCT02781727, "A Phase 3 Trial of the Safety, Tolerability and Efficacy of TransCon hGH Weekly Versus Daily hGH in Children With Growth HormoneDeficiency (GHD)," ClinicalTrials.gov archive, submitted Dec. 6, 2021.
History of Changes for Study: NCT03305016, "A Safety, Tolerability and Efficacy Study of TransCon hGH in Children with Growth Hormone Deficiency," ClinicalTrials.gov archive, submitted Dec. 7, 2021.
Lal, "Perspectives on long-acting growth hormone therapy in children and adults," Arch Endocrinol Metab., 63/6, (Sep. 2019).
Miccoli et al., "Height Outcome of Recombinant Human Growth Hormone Treatment in Achondroplasia Children: A Meta-Analysis," Horm Res Paediatr, DOI: 10.1159/000446958 (Jun. 2016).
Pan et al., "Effect of recombinant human growth hormone on liver fat content in young adults with nonalcoholic fatty liver disease," Clinical Endocrinology., vol. {0} 94, No. {0} 2, Feb. 1, 2021 (Feb. 1, 2021), p. 183-192, Abstract only.
Takahashi et al., "Growth Hormone Reverses Nonalcoholic Steatohepatitis in a Patient With Adult Growth Hormone Deficiency," Gastroenterology, 32:938-943, (Mar. 2007).
Takahashi, "The Role of Growth Hormone and Insulin-Like Growth Factor-I in the Liver," Int. J. Mol. Sci, 18, 1447, https://doi.org/10.3390/ijms18071447, (2017).
Thornton et al., "Weekly Lonapegsomatropin in Treatment-Naïve Children With Growth Hormone Deficiency: The Phase 3 heiGHt Trial," The Journal of Clinical Endocrinology & Metabolism, vol. 106, No. 11, 3184-3195, (Jul. 2021).
Verzijl et al., "Pegbelfermin (BMS-986036): an investigational PEGylated fibroblast growth factor21 analogue for the treatment of nonalcoholic steatohepatitis," Epert Opinion on Investigational Drugs, vol. 27, No. 2, 125-133, https://doi.org/10.1080/13543784.2020.1708898 (2020).
U.S. Appl. No. 16/866,764, Non-Final Office Action mailed Feb. 14, 2024.
U.S. Appl. No. 17/006,589, Non-Final Office Action mailed Jan. 5, 2024.
U.S. Appl. No. 17/006,589, Notice of Allowance and Interview Summary mailed Jun. 20, 2024.
U.S. Appl. No. 17/215,991, Notice of Allowance mailed Mar. 13, 2024.
U.S. Appl. No. 15/528,350, Notice of Allowance mailed Feb. 23, 2024.
U.S. Appl. No. 17/215,991, Non-Final Office Action mailed Jun. 20, 2024.
WIPO Application No. PCT/EP2022/058584, PCT International Preliminary Report on Patentability mailed Oct. 3, 2023.
WIPO Application No. PCT/EP2022/058584, PCT International Search Report and Written Opinion of the International Searching Authority mailed Jun. 17, 2022.
Dyson, "Khimiya sintetitcheskikh lekarstvennykh veshhestv (May's Chemistry of synthethic drugs)," Lang., Moscow: "Mir", 1964, p. 12-19, English translation.
Populyarnaya medicinskaya enciklopediya, gl. Red. V. I. Pokrovskij, 4-e izd., UI. "Knigochej", 1997, str. 317 (lekarstvennye sredstva) (= Popular medical encyclopedia, chief editor V. I. Pokrovskij, fourth edition, "Knigochej", 1997, p. 317 (drugs) English translation.
U.S. Appl. No. 15/528,350, Notice of Allowance mailed Oct. 27, 2023.

* cited by examiner

SEQUENCE LISTING

<160> NUMBER OF SEQ ID NOS: 2

<210> SEQ ID NO 1
<211> LENGTH: 191
<212> TYPE: PRT

<213> ORGANISM: Homo sapiens

<400> SEQUENCE: 1

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 2
<211> LENGTH: 191
<212> TYPE: PRT
<213> ORGANISM: Artificial Sequence
<220> FEATURE:
<223> OTHER INFORMATION: L101C mutant of human growth hormone

<400> SEQUENCE: 2

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Cys Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160
```

```
Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
        180                 185                 190
```

LONG-ACTING GROWTH HORMONE DOSAGE FORMS WITH SUPERIOR EFFICACY TO DAILY SOMATROPIN

RELATED APPLICATIONS

The present application is a § 371 National Stage filing of PCT International Application No. PCT/EP2020/055513, filed Mar. 3, 2020, which claims the benefit of EP patent application Ser. No. 19/160,459.4, filed on Mar. 4, 2019. The entirety of each application is incorporated herein by reference thereto.

The present invention relates to a long-acting growth hormone or a pharmaceutical formulation comprising such long-acting growth hormone for use in a method of treating growth hormone deficiency with improved outcomes.

Human growth hormone (hGH) is widely used for the treatment of short stature resulting from GH deficiency (GHD) or insufficiency as well as other growth disorders. Growth hormone (GH) is currently only available in most territories as formulations requiring daily injections.

Prescription practices for daily growth hormone formulations indicate that dosing should be individualized based on the weight and growth response of each patient. Typical doses range from 0.17 mg/kg/week to 0.30 mg/kg/week for growth hormone deficient children.

Noncompliance with growth hormone therapy is widespread. Noncompliance with current hGH treatment is frequent since the drug needs to be injected daily over many years, and daily injections are perceived invasive by the patients. Noncompliance has a proven negative impact on the outcomes of treatment. Ease of use of the injection device, the features of injection devices as well as the frequency of injection may play an important role in compliance.

To improve compliance and treatment outcomes, several companies have developed technologies for creating long-acting growth hormone products.

Nutropin Depot® was the first long-acting growth hormone to be approved and was based on encapsulation of growth hormone in biodegradable microparticles. Nutropin Depot was available on the US market, but was withdrawn in 2004.

Nutropin Depot was intended for once-monthly or twice-monthly injections at a dose of 1.5 mg/kg/month or 0.75 mg/kg/twice monthly. In clinical studies, Nutropin Depot increased annual height velocity in growth hormone deficient children, but comparison to historical studies showed growth rates achieved on daily therapy were higher than on Nutropin Depot.

Somatropin Biopartners, has been approved by the European Medicines Agency, but was since withdrawn from use in the European Union. Somatropin Biopartners is a long-acting growth hormone based on encapsulation of growth hormone in biodegradable microparticles. Somatropin Biopartners is indicated for weekly administration. Clinical trials have demonstrated that dosing of pediatric patients with growth hormone deficiency at a dose of 0.5 mg/kg/week results in height velocities comparable to daily growth hormone dose at 0.21 mg/kg/week, given as seven daily injections.

Of the approved long-acting growth hormones, none have demonstrated superior efficacy compared to an equimolar dose of daily somatropin. In addition to the two long-acting growth hormone preparations that have received regulatory approval in Western countries, there are a number of long-acting growth hormone preparations in development.

For example, VRS-317 was studied in a phase 3 clinical trial in pediatric GHD patients. Patients administered with somavaratan twice a month were found to have an annualized height velocity (AHV) of 9.44 cm, while it was 10.7 cm in the case of patients treated with Genotropin daily. The results showed that the trial did not meet the primary endpoint of non-inferiority for primary efficacy variable, annual height velocity, compared to daily growth hormone Genotropin dosed at 0.24 mg/kg/week.

Somatrogon (MOD-4023, hGH-CTP) is dosed in a phase 2 dose range study in pediatric GHD patients using a dose regimen at weekly intervals. Specifically, patients were dosed with a dose of 0.25 mg/kg/week; 0.48 mg/kg/week or 0.66 mg/kg/week. The dose of 0.66 mg/kg/week is expected to provide comparable efficacy to daily growth hormone and has been selected for further study in a Phase 3 clinical trial, comparing efficacy to daily somatropin dosed at 0.24 mg/kg/week.

TV-1106 (albutropin) is being studied in a phase 2 dose range study in pediatric GHD patients employing a weekly fixed dose regimen. Specifically, patients were dosed with a fixed dose of 0.554 mg/kg/week; 0.924 mg/kg/week or 1.20 mg/kg/week. Neutralizing antibodies to TV-1106 have been detected, and development of TV-1106 has been discontinued.

Somapacitan (NNC0195-0092) has been studied in a dose range study in growth hormone deficient children. The trial compared three somapacitan doses (0.04, 0.08 or 0.16 mg/kg/week) to daily somatropin at 0.24 mg/kg/week. Annualized height velocity did not differ significantly for the 0.08 and 0.16 mg/kg/week doses compared to daily somatropin, whereas the low dose was inferior. The mean annualized height velocity for the three dose levels of somapacitan was 8.0 cm, 10.9 cm and 12.9 cm, respectively, and for the two highest doses comparable to 11.4 cm for daily somatropin.

Of the long-acting growth hormones in clinical development, none have demonstrated superior efficacy compared to an equimolar dose of daily somatropin. In addition, several have failed to demonstrate comparable efficacy to daily somatropin in phase 3 clinical trials.

Furthermore, treatment with growth hormone also faces a certain percentage of non-responders, i.e. patients that do not respond with adequately increased AHV compared to patients not receiving growth hormone treatment, which is unsatisfactory for the patient. Therefore, there is a need for reducing the number of non-responders.

In summary, despite several attempts it has not been possible to develop a long-acting growth hormone that demonstrates superior efficacy outcomes compared to daily somatropin. There is also a need for a long-acting growth hormone that provides superior efficacy to daily somatropin with an increased percentage of responders, which may help patients in need of growth hormone therapy to attain best therapeutic treatment outcomes.

It is therefore an object of the present invention to at least partially overcome the shortcomings described above.

This object is achieved with a long-acting growth hormone or a pharmaceutical formulation comprising the long-acting growth hormone, wherein administration of the long-acting growth hormone or the pharmaceutical formulation to patients with growth hormone deficiency leads to superior efficacy compared to administration of an equimolar amount of a daily somatropin.

In another aspect the present invention relates to a long-acting growth hormone or a pharmaceutical composition comprising the long-acting growth hormone for use in a method of treating growth hormone deficiency with superior efficacy.

In another aspect the present invention relates to a method of treating a patient suffering from a growth hormone deficiency, the method comprising the step of administering an effective amount of a long-acting growth hormone or a pharmaceutical composition comprising such long-acting growth hormone to the patient, wherein said method of treating leads to superior efficacy.

In another aspect the present invention relates to a long-acting growth hormone or a pharmaceutical formulation comprising the long-acting growth hormone, wherein said long-acting growth hormone or the pharmaceutical formulation comprises a dose of 0.24 mg/kg/week growth hormone or growth hormone equivalents and administration of said long-acting growth hormone formulation to patients with growth hormone deficiency leads to superior efficacy compared to administration of a dose of 0.24 mg/kg/week of a daily somatropin.

In another aspect the present invention relates to a long-acting growth hormone or a pharmaceutical formulation comprising the long-acting growth hormone for use in a method of treating, wherein said long-acting growth hormone or the pharmaceutical formulation is administered in a dose of 0.24 mg/kg/week growth hormone or growth hormone equivalents and administration of said long-acting growth hormone pharmaceutical composition comprising said long-acting growth hormone leads to superior efficacy compared to administration of a dose of 0.24 mg/kg/week of a daily somatropin.

In another aspect the present invention relates to a method of treating a patient suffering from a growth hormone deficiency, the method comprising the step of administering a dose of 0.24 mg/kg/week growth hormone or growth hormone equivalents of a long-acting growth hormone or a pharmaceutical formulation comprising the long-acting growth hormone, wherein such treatment results in superior efficacy compared to administration of a dose of 0.24 mg/kg/week of a daily somatropin.

It is understood that the phrase "of a dose of 0.24 mg/kg/week of a daily somatropin" means that the accumulated dose of daily somatropin after one week of administration is 0.24 mg/kg, meaning that the daily dose of such daily somatropin is (0.24 mg/kg/week)/(7 days/week)=0.343 mg/day (rounded).

In another aspect the present invention relates to a long-acting growth hormone or a pharmaceutical formulation comprising such long-acting growth hormone for use in the treatment of growth hormone deficiency, wherein said treatment increases IGF-1 levels in plasma by a standard deviation score (SDS) of at least 0.2 more than the equivalent dose of daily hGH.

In another aspect the present invention relates to a method of treating growth hormone deficiency, the method comprising the step of administering an effective amount of a long-acting growth hormone or a pharmaceutical composition comprising such long-acting growth hormone to a patient in need thereof, wherein said treating said growth hormone deficiency increases IGF-1 levels in plasma by a SDS of at least 0.2 more than the equivalent dose of daily hGH.

It is understood that an SDS may either be calculated at the level of a patient population or may be calculated for an individual patient by comparing said patient's data to data from a respective patient population available in the literature. In certain embodiments the increase is at least 0.25 SDS. In certain embodiments the increase is at least 0.3 SDS. In certain embodiments the increase is at least 0.35 SDS. In certain embodiments the increase is at least 0.4 SDS.

In another aspect the present invention relates to a long-acting growth hormone or a pharmaceutical formulation comprising such long-acting growth hormone for use in a method of reducing the percentage of non-responders in a patient population suffering from growth hormone deficiency.

In another aspect the present invention relates to a method of reducing the percentage of non-responders among a patient population suffering from a growth hormone deficiency, the method comprising the step of administering an effective amount of a long-acting growth hormone or a pharmaceutical formulation comprising such long-acting growth hormone of the present invention to a patient of said patient population.

In certain embodiments the percentage of non-responders is reduced to less than 10%. In certain embodiments the percentage of non-responders is reduced to less than 9%. In certain embodiments the percentage of non-responders is reduced to less than 8%. In certain embodiments the percentage of non-responders is reduced to less than 7%. In certain embodiments the percentage of non-responders is reduced to less than 6%. In certain embodiments the percentage of non-responders is reduced to less than 5%. In certain embodiments the percentage of non-responders is reduced to less than 4%.

In another embodiment the present invention relates to a long-acting growth hormone or a pharmaceutical composition comprising said long-acting growth hormone for use in a method of treating non-responders of growth hormone treatment. In other words, the present invention relates to a long-acting growth hormone or a pharmaceutical composition comprising such long-acting growth hormone for use in the treatment of a growth hormone deficiency in a patient, wherein the patient is a non-responder. In certain embodiments such non-responders have previously been treated with daily growth hormone.

In another aspect the present invention relates to a method of treating growth hormone deficiency in non-responders, the method comprising the step of administering an effective amount of a long-acting growth hormone or a pharmaceutical composition comprising such long-acting growth hormone to a patient in need thereof. In certain embodiments such patient is a patient previously treated with daily growth hormone.

In another aspect the present invention relates to a long-acting growth hormone or a pharmaceutical formulation comprising such long-acting growth hormone for use in a method of increasing the percentage of responders in a patient population suffering from growth hormone deficiency.

In another aspect the present invention relates to a method of increasing the percentage of responders in a patient population suffering from a growth hormone deficiency, the method comprising the step of administering an effective amount of the long-acting growth hormone or a pharmaceutical composition comprising such long-acting growth hormone to a patient of said patient population.

In certain embodiments the percentage of responders is increased to at least 90%. In certain embodiments the percentage of responders is increased to at least 91%. In certain embodiments the percentage of responders is increased to at least 92%. In certain embodiments the percentage of responders is increased to at least 93%. In certain embodiments the percentage of non-responders is increased to at least 94%. In certain embodiments the percentage of non-responders is increased to at least 95%. In certain embodiments the percentage of non-responders is increased to at least 96%.

It was surprisingly found that the equimolar administration of a long-acting growth hormone was able to provide superior annual height velocity (AHV) to daily somatropin.

It was surprisingly found that providing a long-acting growth hormone with a PK profile that provides sustained exposure over the course of the administration frequency was associated with superior AHV.

It is hypothesized that the PK profile of released hGH from TransCon hGH may lead to improved engagement of growth hormone receptors in target tissues, which resulted in higher AHV and IGF-1 levels compared to daily hGH at the same dose.

The superior AHV may be explained by the delivery pattern of hGH to the peripheral tissue following sustained hGH release from long-acting growth hormone compared to intermittent exposure following daily hGH administration.

The pharmacodynamic effect of intermittent versus continuous hGH exposure in target tissue has been studied in healthy adults where hGH was delivered either by continuous infusion or by pulsatile delivery. Human growth hormone infusion was about twice as effective at increasing both plasma IGF-I concentration and IGF-I mRNA in muscle compared to pulsatile GH exposure (Surya et al., J Clin Endocrinol Metab 94: 2828-2834, 2009). These data are supported by studies in growth hormone deficient adults, where continuous infusion of GH was associated with significantly higher IGF-1 levels compared to bolus injections at an equivalent daily dose (Jorgensen et al., The Journal of Clinical Endocrinology & Metabolism, Volume 70, Issue 6, 1 Jun. 1990, Pages 1616-1623, Laursen et al., J Clin Endocrinol Metab 86:1222-1228, 2001). However, no difference in clinical outcomes were observed in this study.

Administration of a long-acting growth hormone with a PK profile that provides sustained exposure over the course of the administration frequency was surprisingly associated with superior AHV. Previously, a long-acting growth hormone based on PLGA encapsulation of growth hormone, Nutropin Depot, failed to demonstrate a superior treatment outcome in children with GHD. In fact, compared to historical controls, growth rates achieved on daily growth hormone therapy were higher than on Nutropin Depot. In addition, when patients on daily growth hormone therapy were switched to Nutropin Depot, they experienced a decrease in growth rates, that was of a higher magnitude than what could be accounted for by the normal decrease experience by patients remaining on daily growth hormone therapy. The PK profile for Nutropin Depot may not have been optimized, as approximately 50-60% of the GH exposure occurred during the first 2 d and growth hormone levels returning to baseline before the next injection (J Clin Endocrinol Metab, October 2001, 86(10):4700-4706; J Clin Endocrinol Metab, July 2004, 89(7):3234-3240).

It was also surprisingly found that the equimolar administration of a long-acting growth hormone was able to provide a reduced rate of non-responders compared to daily somatropin.

Within the present invention the terms are used with the meaning as follows:

As used herein, the term "human growth hormone (hGH)" refers all hGH polypeptides, preferably from mammalian species, more preferably from human and mammalian species, more preferably from human and murine species, as well as their variants, analogs, orthologs, homologs, and derivatives and fragments thereof, that are characterized by promoting growth in the growing phase and in maintaining normal body composition, anabolism, and lipid metabolism. Preferably, the term "hGH" refers to the hGH polypeptide of SEQ ID NO:1 as well as its variants, homologs and derivatives exhibiting essentially the same biological activity, i.e. promoting growth in the growing phase and in maintaining normal body composition, anabolism, and lipid metabolism. More preferably, the term "hGH" refers to the polypeptide of SEQ ID NO:1.

SEQ ID NO:1 has the following sequence:

FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF

As used herein, the term "somatropin" refers to a polypeptide with the sequence of SEQ ID NO:1

As used herein, the term "hGH polypeptide variant" refers to a polypeptide from the same species that differs from a reference hGH polypeptide. Preferably, such reference hGH polypeptide sequence is the sequence of SEQ ID NO:1. Generally, differences are limited so that the amino acid sequence of the reference and the variant are closely similar overall and, in many regions, identical. Preferably, hGH polypeptide variants are at least 70%, 80%, 90%, 95%, 96%, 97%, 98% or 99% identical to a reference hGH polypeptide, preferably the hGH polypeptide of SEQ ID NO:1. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:1.

Such hGH polypeptide variants may be naturally occurring variants, such as naturally occurring allelic variants encoded by one of several alternate forms of a hGH occupying a given locus on a chromosome or an organism, or isoforms encoded by naturally occurring splice variants originating from a single primary transcript. Alternatively, a hGH polypeptide variant may be a variant that is not known to occur naturally and that can be made mutagenesis techniques known in the art.

It is known in the art that one or more amino acids may be deleted from the N-terminus or C-terminus of a bioactive peptide or protein without substantial loss of biological function.

It is also recognized by one of ordinary skill in the art that some amino acid sequences of hGH polypeptides can be varied without significant effect of the structure or function of the protein. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term hGH polypeptide also encompasses all hGH polypeptides encoded by hGH analogs, orthologs, and/or species homologs. As used herein, the term "hGH analog" refers to hGH of different and unrelated organisms which perform the same functions in each organism, but which did not originate from an ancestral structure that the organisms' ancestors had in common. Instead, analogous hGHs arose separately and then later evolved to perform the same or similar functions. In other words, analogous hGH polypeptides are polypeptides with quite different amino acid sequences but that perform the same biological activity, namely promoting growth in the growing phase and maintaining normal body composition, anabolism, and lipid metabolism.

As used herein the term "hGH ortholog" refers to hGH within two different species which sequences are related to each other via a common homologous hGH in an ancestral species, but which have evolved to become different from each other.

As used herein, the term "hGH homolog" refers to hGH of different organisms which perform the same functions in each organism, and which originate from an ancestral structure that the organisms' ancestors had in common. In other words, homologous hGH polypeptides are polypeptides with quite similar amino acid sequences that perform the same biological activity, namely promoting growth in the growing phase and maintaining normal body composition, anabolism, and lipid metabolism. Preferably, hGH polypeptide homologs may be defined as polypeptides exhibiting at least 40%, 50%, 60%, 70%, 80%, 90%, 95%, 96%, 97%, 98% or 99% identity to a reference hGH polypeptide, preferably the hGH polypeptide of SEQ ID NO:1.

Thus, a hGH polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the hGH polypeptide is fused with another compound, such as a compound to increase the half-life of the polypeptide (for example, polyethylene glycol); and/or (iv) one in which additional amino acids are fused to the hGH polypeptide, such as an IgG Fc fusion region peptide or leader or secretory sequence or a sequence which is employed for purification of the above form of the polypeptide or a pre-protein sequence.

The hGH polypeptide may be a monomer or multimer. Multimers may be dimers, trimers, tetramers or multimers comprising at least five monomeric polypeptide units. Multimers may also be homodimers or heterodimers. Multimers of the invention may be the result of hydrophobic, hydrophilic, ionic and/or covalent association and/or may be indirectly linked, by for example, liposome formation. Preferably, the hGH polypeptide is a monomer.

As used herein, the term "hGH polypeptide fragment" refers to any peptide or polypeptide comprising a contiguous span of a part of the amino acid sequence of a hGH polypeptide, preferably the polypeptide of SEQ ID NO:1.

More specifically, a hGH polypeptide fragment comprises at least 6, preferably at least 8 or 10, more preferably at least 12, 15, 20, 25, 30, 35, 40, 50, 60, 75, 100, 125, 150, 175, 191 consecutive amino acids of a hGH polypeptide, more preferably of the polypeptide of SEQ ID NO:1. A hGH polypeptide fragment may additionally be described as sub-genuses of hGH polypeptides comprising at least 6 amino acids, wherein "at least 6" is defined as any integer between 6 and the integer representing the C-terminal amino acid of a hGH polypeptide, preferably of the polypeptide of SEQ ID No:1. Further included are species of hGH polypeptide fragments at least 6 amino acids in length, as described above, that are further specified in terms of their N-terminal and C-terminal positions. Also encompassed by the term "hGH polypeptide fragment" as individual species are all hGH polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a hGH polypeptide, preferably the hGH polypeptide of SEQ ID:NO1, is included in the present invention.

It is noted that the above species of polypeptide fragments may alternatively be described by the formula "a to b"; where "a" equals the N-terminal most amino acid position and "b" equals the C-terminal most amino acid position in the polynucleotide; and further where "a" equals an integer between 1 and the number of amino acids of a hGH polypeptide sequence minus 6, and where "b" equals an integer between 7 and the number of amino acids of the hGH polypeptide sequence; and where "a" is an integer smaller then "b" by at least 6, preferably of the hGH polypeptide sequence of SEQ ID NO:1.

As used herein the term "long-acting growth hormone" or "long-acting growth hormone compound" refers to a compound which comprises hGH either in crystallized form or wherein the hGH is embedded, fused or conjugated to at least one other chemical compound or moiety, such as for example a polymer or fatty acid-derived moiety, and has an increased retention time in a patient's body compared to unmodified hGH. The retention time is the time between two consecutive administrations in which the concentration in plasma of unmodified hGH, such as the hGH of SEQ ID NO:1 or SEQ ID NO:2, is at a therapeutically effective concentration. In certain embodiments such therapeutic effective level is a concentration of at least 2 ng hGH/ml plasma. For hGH the retention time is about 12 hours. In certain embodiments the retention time for a long-acting growth hormone is at least 24 hours. In certain embodiments the retention time for a long-acting growth hormone is at least 36 hours. In certain embodiments the retention time for a long-acting growth hormone is at least 48 hours. In certain embodiments the retention time for a long-acting growth hormone is at least 72 hours.

It is understood that also the time between two consecutive administrations of the long-acting growth hormone is increased compared to standard treatment with hGH, which is administered once a day. In certain embodiments the time between two consecutive administrations is at least 2 days. In certain embodiments the time between two consecutive administrations is at least 3 days. In certain embodiments the time between two consecutive administrations is at least 4 days. In certain embodiments the time between two consecutive administrations is at least 5 days. In certain embodiments the time between two consecutive administrations is at least 6 days. In certain embodiments the time between two consecutive administrations is 1 week. In certain embodiments the time between two consecutive administrations is 2 weeks. In certain embodiments the time between two consecutive administrations is 4 weeks.

In certain embodiments the dose administered with each administration is at least 0.16 mg/kg/week. In certain embodiments the dose ranges from 0.16 mg/kg/week to 0.4 mg/kg/week such as from 0.24 mg/kg/week to 0.3 mg/kg/week. In certain embodiments the dose is 0.24 mg/kg/week. In certain embodiments the dose is 0.3 mg/kg/week.

In certain embodiments the therapeutically effective concentration is achieved for at least 50% of the dosing interval, i.e. a therapeutically effective concentration is achieved for at least 50% of the time period between two consecutive administrations of the long-acting growth hormone.

As used herein, the term "drug" refers to a substance used in the treatment, cure, prevention or diagnosis of a disease or used to otherwise enhance physical or mental well-being of a patient. If a drug is conjugated to another moiety, the moiety of the resulting product that originated from the drug is referred to as "drug moiety" or "biologically active moiety".

As used herein the term "prodrug" refers to a biologically active moiety reversibly and covalently connected to a specialized protective group through a reversible prodrug linker moiety comprising a reversible linkage with the biologically active moiety to alter or to eliminate undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug.

As used herein the terms "growth hormone equivalent" and "hGH equivalent" refer to the total mass of hGH or hGH moieties comprised in a long-acting growth hormone compound. In other words, if the long-acting growth hormone compound is for example a prodrug in which the hGH moiety is reversibly conjugated to a polymer the term "growth hormone equivalent" refers to the total mass of hGH moieties, but not to the total mass of hGH prodrug. If the long-acting growth hormone compound is for example a fusion protein in which the hGH moiety is fused with an natural or unnatural amino acid sequence the term "growth hormone equivalent" refers to the total mass of hGH moieties, but not to the total mass of the fusion protein.

As used herein the term "equimolar" means having the same amount of moles.

The terms "formulation", "pharmaceutical formulation", "composition" and "pharmaceutical composition" are used synonymously and refer to a combination of one or more long-acting hGH and one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. In certain embodiments the terms formulation", "pharmaceutical formulation", "composition" and "pharmaceutical composition" refer to at least one long-acting hGH and at least one excipient.

As used herein the term "liquid formulation" means a formulation comprising long-acting hGH and at least one solvent. A preferred solvent is water.

As used herein the term "dry formulation" means that the long-acting acting growth hormone is provided in dry form. Suitable methods for drying are spray-drying and lyophilization which is also referred to as freeze-drying. Such dry formulation has a residual water content of a maximum of 10%, preferably less than 5% and more preferably less than 2% which residual water content is determined according to Karl Fischer. The preferred method of drying is lyophilization. "Lyophilized formulation" means that the dry formulation was first frozen and subsequently subjected to water reduction by means of reduced pressure. This terminology does not exclude additional drying steps which may occur in the manufacturing process prior to filling the formulation into the final container.

As used herein the term "reconstituted formulation" means the result of adding a solvent which is also referred to as "reconstitution solution" to a dry formulation. Preferably, the amount of solvent is such that the dry formulation is completely dissolved in the resulting reconstituted formulation.

As used herein, the term "superior" refers to a statistically significant better therapeutic outcome, for example with regard to AHV. In certain embodiments "statistically significant better" is defined as a p-value of less than 0.05, such as a p-value of less than 0.01, using a suitable statistical model. In certain embodiments such statistical model is analysis of variance (ANOVA). In certain embodiments such statistical model is analysis of covariance (ANCOVA).

As used herein the term "unit dosage" refers to the amount of drug, in particular of long-acting growth hormone formulation, which constitutes one dose, i.e. the amount of drug, in particular long-acting growth hormone formulation, which corresponds to one administration.

As used herein the term "unit dosage form" refers to a presentation of a unit dosage, i.e. refers to any application device comprising a unit dose of drug, in particular of long-acting growth hormone formulation. A preferred application device is selected from the group consisting of a syringe with needle, injection pen, autoinjector pen, needle-free injector, electronic injector and dual chamber cartridge.

As used herein the term "efficacy" refers to both the annualized height velocity achieved in naïve growth hormone children and responder rate.

As used herein, a "pharmaceutically effective dose" refers to that amount of growth hormone or growth hormone equivalent sufficient to treat growth hormone deficiency.

As used herein, the term "responder" refers to a growth hormone deficiency patient receiving growth hormone therapy and having annualized height velocity above 8.0 cm per year.

As used herein, the term "non-responder" refers to a growth hormone deficiency patient receiving growth hormone therapy and having annualized height velocity less than 8.0 cm per year. It is understood that said growth hormone therapy is the standard therapy with human growth hormone, such as daily administration of a human growth hormone of SEQ ID NO:1, in a dose ranging in certain embodiments from 0.17 mg/kg/week to 0.30 mg/kg/week. Exemplary doses are 0.24 mg/kg/week and 0.3 mg/kg/week of the hGH of SEQ ID NO:1.

As used herein, the term "annualized height velocity" or "annual height velocity" ("AHV") is defined as the difference in height at treatment initiation and about 12 months thereafter.

As used herein the term "about" in combination with a numerical value is used to indicate a range ranging from and including the numerical value plus and minus no more than 10%, more preferably no more than 8%, even more preferably no more than 5% and most preferably no more than 2%. For example, the phrase "about 20%" is used to mean a range ranging from and including 20%+/−10%, preferably 20%+/−8%, even more preferably 20%+/−5% and most preferably 20%+/−2%.

As used herein, the term "excipient" refers to a diluent, adjuvant, or vehicle with which the therapeutic is administered.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "moiety" means a part of a molecule, which lacks at least one atom compared to the corresponding reagent. If, for example, a reagent of the formula "H—X—H" reacts with another reagent and becomes part of the reaction product, the corresponding moiety of the reaction product has the structure "H—X—" or "—X—" whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R)—" can be attached to two moieties or interrupting a moiety either as "—C(O)N(R)—" or as "—N(R)C(O)—". Similarly, a moiety

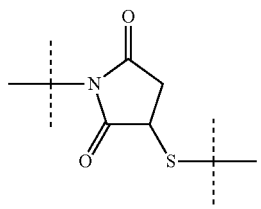

can be attached to two moieties or can interrupt a moiety either as

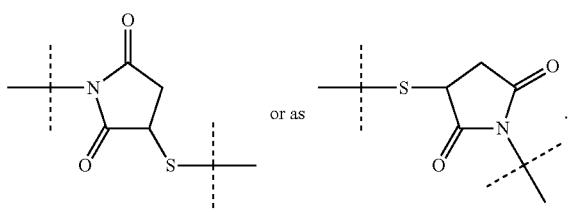

In case the long-acting growth hormone comprises one or more acidic or basic groups, the invention also comprises their corresponding pharmaceutically or toxicologically acceptable salts, in particular their pharmaceutically utilizable salts. Thus, the long-acting growth hormone which comprises acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Long-acting growth hormone which comprises one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the long-acting growth hormone simultaneously comprises acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of long-acting growth hormone, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMA (Europe) and/or the FDA (US) and/or any other national regulatory agency for use in animals, preferably in humans.

As used herein, the terms "reversible", "reversibly", "degradable" or "degradably" with regard to the attachment of a first moiety to a second moiety means that the linkage that connects said first and second moiety is cleavable under physiological conditions, which physiological conditions are aqueous buffer at pH 7.4 and 37° C., with a half-life ranging from one day to one month, such as from two days to three weeks, such as from three days to two weeks. Accordingly, the term "stable" with regard to the attachment of a first moiety to a second moiety means that the linkage that connects said first and second moiety exhibits a half-life of more than one month under physiological conditions.

As used herein, the term "water-insoluble" refers to a compound of which less than 1 g can be dissolved in one liter of water at 20° C. to form a homogeneous solution. Accordingly, the term "water-soluble" refers to a compound of which 1 g or more can be dissolved in one liter of water at 20° C. to form a homogeneous solution.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as crosslinked hydrogels, no meaningful molecular weight ranges can be provided.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

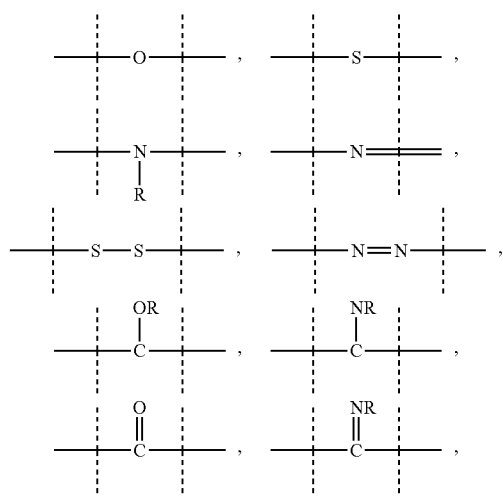

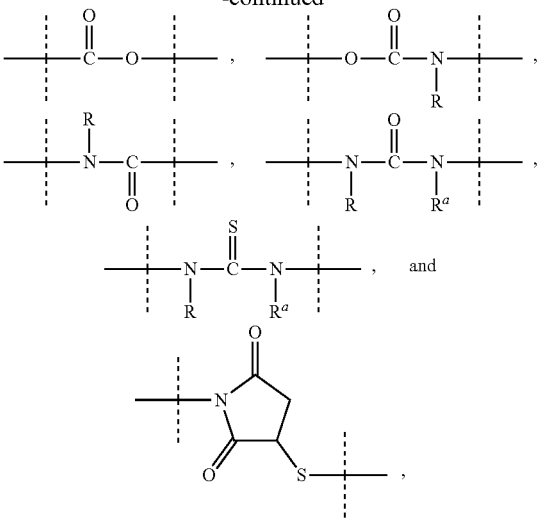

wherein dashed lines indicate attachment to the remainder of the moiety or reagent, and R and $R^a$ are independently of each other selected from the group consisting of H, methyl, ethyl, propyl, butyl, pentyl and hexyl.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$), and —OC(O)N(R$^{x3}$);

R$^{x1}$, R$^{x1a}$, R$^{x1b}$ are independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more R$^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more $R^{x2}$ which are the same or different;

each $R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each R, $R^{x3a}$, $R^{x4}$, $R^{x4a}$, $R^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-10}$ alkyl, $C_{2-10}$ alkenyl, and $C_{2-10}$ alkynyl; wherein -T$^0$, $C_{1-10}$ alkyl, $C_{2-10}$ alkenyl, and $C_{2-10}$ alkynyl are optionally substituted with one or more $R^{x2}$, which are the same or different and wherein $C_{1-10}$ alkyl, $C_{2-10}$ alkenyl, and $C_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$), and —OC(O)N(R$^{x3}$)—;

each $R^{x1}$, $R^{x1a}$, $R^{x1b}$, $R^{x3}$, $R^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more $R^{x2}$ which are the same or different;

each $R^{x2}$ is independently selected from the group consisting of halogen, —CN, oxo (=O), —COOR$^{x4}$, —OR$^{x4}$, —C(O)R$^{4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each $R^{x4}$, $R^{x4a}$, $R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1}$), —OC(O)N(R$^{x1}$R$^{x1a}$), -T$^0$, $C_{1-6}$ alkyl, $C_{2-6}$ alkenyl, and $C_{2-6}$ alkynyl; wherein -T$^0$, $C_{1-6}$ alkyl, $C_{2-6}$ alkenyl, and $C_{2-6}$ alkynyl are optionally substituted with one or more $R^{x2}$, which are the same or different and wherein $C_{1-6}$ alkyl, $C_{2-6}$ alkenyl, and $C_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each $R^{x1}$, $R^{x1a}$, $R^{x1b}$, $R^{x2}$, $R^{x3}$, $R^{x3a}$ is independently selected from the group consisting of —H, halogen, $C_{1-6}$ alkyl, $C_{2-6}$ alkenyl, and $C_{2-6}$ alkynyl;

each T$^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T$^0$ is independently optionally substituted with one or more $R^{x2}$, which are the same or different.

Preferably, a maximum of 6-H atoms of an optionally substituted molecule or moiety are independently replaced by a substituent, e.g. 5-H atoms are independently replaced by a substituent, 4-H atoms are independently replaced by a substituent, 3-H atoms are independently replaced by a substituent, 2-H atoms are independently replaced by a substituent, or 1-H atom is replaced by a substituent.

The term "spacer" as used herein refers preferably to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —N(R$^{z1}$)—, —OC(OR$^{z1}$)(R$^{z1a}$)—, —N(R$^{z1}$)C(O)N(R$^{z1a}$)—, —OC(O)N(R$^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —S—, —N(R$^{z3}$)—, —OC(OR$^{z3}$)(R$^{z3a}$)—, —N(R$^{z3}$)C(O)N(R$^{z3a}$)—, and —OC(O)N(R$^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^{z4}$)—, —S(O)$_2$N(R$^{z4}$)—, —S(O)N(R$^{z4}$)—, —S(O)$_2$—, —S(O)—, —N(R$^{z4}$)S(O)$_2$N(R$^{z4a}$)—, —N(R$^{z4}$)—, —OC(OR$^{z4}$)(R$^{z4a}$)—, —N(R$^{z4}$)C(O)N(R$^{z4a}$)—, and —OC(O)N(R$^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^2$, which are the same or different;

each $R^z$ is independently selected from the group consisting of halogen, —CN, oxo (=O), —COOR$^{z5}$, —OR$^{z5}$, —C(O)R$^{z5}$, —C(O)N(R$^{z5}$R$^{z5a}$), —S(O)$_2$N ($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, the term "spacer" refers to a moiety selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^3$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different; and each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl, wherein $C_{1-6}$ alkyl is optionally substituted with one or more halogen, which are the same or different.

Even more preferably, the term "spacer" refers to a moiety selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $R^{z2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each $R^{z2}$ is independently selected from the group consisting of halogen, and $C_{1-6}$ alkyl; and each $R^{z3}$, $R^{z3a}$, $R^{z4}$, $R^{z4a}$, $R^{z5}$, $R^{z5a}$ and $R^{z5b}$ is independently of each other selected from the group consisting of —H, and $C_{1-6}$ alkyl; wherein $C_{1-6}$ alkyl is optionally substituted with one or more halogen, which are the same or different.

The term "interrupted" means that a group of atoms is inserted into a moiety between two carbon atoms or—if the insertion is at one of the moiety's ends—between a carbon and a hydrogen atom. It is understood that if a moiety is interrupted by a group of atoms at one of its ends and if the moiety that is interrupted is connected to a second moiety, the interrupting group of atoms may also be so positioned that it is located between the last atom of said moiety and the first atom of the second moiety.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more of the following moieties:

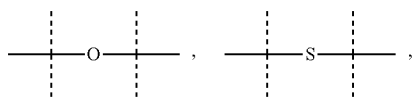

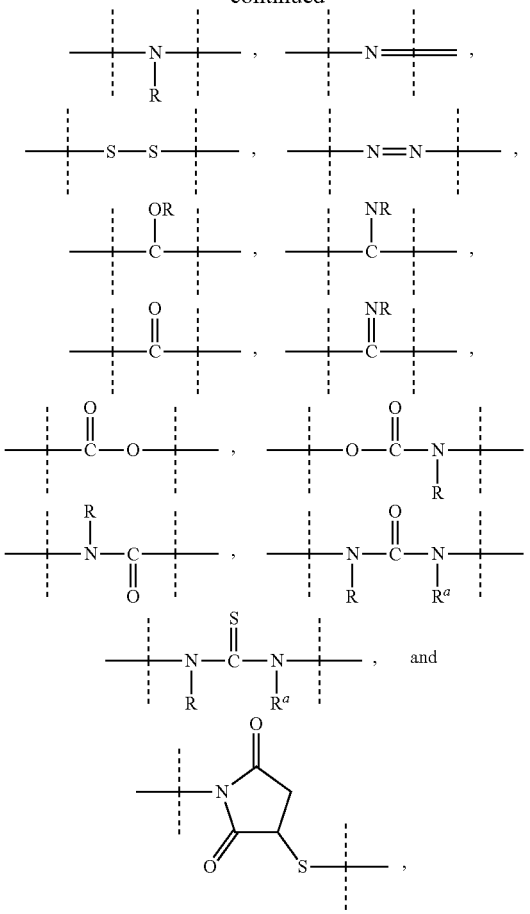

wherein
dashed lines indicate attachment to the remainder of the moiety or reagent; and
R and $R^a$ are independently of each other selected from the group consisting of H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may comprise up to the maximum number of double bonds (aromatic or non-aromatic ring which is fully, partially or un-saturated).

Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may comprise up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may comprise up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may comprise up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

As used herein, "halogen" means fluoro, chloro, bromo or iodo. It is generally preferred that halogen is fluoro or chloro.

In general, the term "comprise" or "comprising" also encompasses "consist of" or "consisting of".

According to the present invention the long-acting growth hormone formulation is provided wherein administration of said long-acting growth hormone formulation to patients with growth hormone deficiency leads to superior efficacy compared to administration of an equimolar dose of a daily somatropin.

In one embodiment the long-acting growth hormone or the pharmaceutical composition comprising said long-acting growth hormone is administered using a syringe with needle.

In another embodiment the long-acting growth hormone or the pharmaceutical composition comprising said long-acting growth hormone is administered using an injection pen.

In another embodiment the long-acting growth hormone or the pharmaceutical composition comprising said long-acting growth hormone is administered using an autoinjector pen.

In another embodiment the long-acting growth hormone or the pharmaceutical composition comprising said long-acting growth hormone is administered using a needle-free injector.

In another embodiment the long-acting growth hormone or the pharmaceutical composition comprising said long-acting growth hormone is administered using an electronic injector.

In another embodiment long-acting growth hormone or the pharmaceutical composition comprising said long-acting growth hormone is administered using a dual chamber cartridge, preferably a dual chamber cartridge that is loaded into a pen device or electronic injector.

In one embodiment the long-acting growth hormone formulation or the pharmaceutical composition comprising said long-acting growth hormone comprises growth hormone embedded or encapsulated in a polymer or lipid-comprising matrix or vehicle. A preferred polymer matrix comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

A preferred polymer is selected from the group consisting of PEG, polylactid-co-glycolid (PLGA) and hyaluronic acid. Most preferably, the polymer is PEG.

In one embodiment the polymer matrix is a hydrogel comprising a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

A preferred hydrogel comprises a polymer selected from the group consisting of PEG, polylactid-co-glycolid (PLGA) and hyaluronic acid. Most preferably, the hydrogel is a PEG-based hydrogel.

In another embodiment the long-acting growth hormone formulation comprises crystalline growth hormone.

In another embodiment the long-acting growth hormone comprises a growth hormone moiety fused to a natural or unnatural amino acid sequence. Preferred amino acid sequences are selected from the group consisting of carboxyl-terminal peptide of the chorionic gonadotropin as described in US 2012/0035101 which are herewith incorporated by reference; albumin; XTEN sequences as described in WO2011123813A2 which are herewith incorporated by reference; proline/alanine random coil sequences as described in WO2011/144756A1 which are herewith incorporated by reference; proline/alanine/serine random coil sequences as described in WO2008/155134 which are herewith incorporated by reference; and Fe fusion proteins. Such fusion may either be stable or reversible.

In another embodiment the long-acting growth hormone comprises a chemically modified growth hormone or an analogue thereof, including PEGylated hGH and hGH modified with fatty acid derivatives. Preferred fatty acid derivatives are those disclosed in WO2005/027978A2 and WO2014/060512A1 which are herewith incorporated by reference. Such chemical modification in the form of a PEG or fatty acid derivative moiety may either be stably or reversibly attached to the hGH moiety. In certain embodiments the chemical modification is a PEG moiety that this stably attached to the hGH moiety. In certain embodiments the chemical modification is a PEG moiety that this reversibly attached to the hGH moiety. In certain embodiments the chemical modification is a fatty acid derivative moiety that this stably attached to the hGH moiety. In certain embodiments the chemical modification is a fatty acid derivative moiety that this reversibly attached to the hGH moiety.

In another embodiment the long-acting growth hormone is a hGH prodrug, in which a hGH moiety is reversibly conjugated to a polymeric or fatty acid-derived moiety. In certain embodiments that the hGH moiety is released in an unmodified form from such hGH prodrug.

Preferably, the long-acting growth hormone is a polymeric hGH prodrug as disclosed in WO05099768 A2 and WO 2009/133137 A2 which are herewith incorporated by reference. Accordingly, the long-acting growth hormone is preferably a polymeric hGH prodrug of formula (Ia) or (Ib)

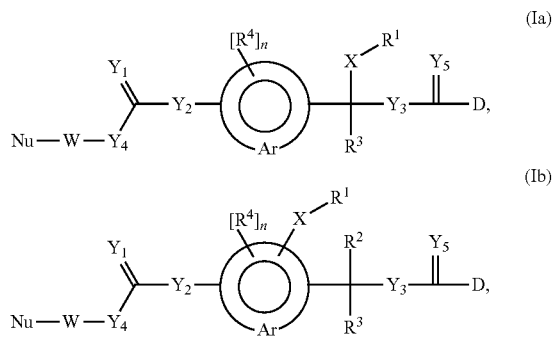

wherein
-D is a hGH moiety connected to the rest of the molecule through an amine functional group;
n is 0, 1, 2, 3, or 4;
—X— is a chemical bond or a spacer;
$=Y_1$, $=Y_5$ are selected independently from the group consisting of $=O$ and $=S$;
—$Y_2$—, —$Y_3$— are selected from the group consisting of —O— and —S—;
—$Y_4$— is selected from the group consisting of —O—, —$NR^5$— and —$C(R^6R^{6a})$—;
—$R^1$ is a carrier, preferably a water-soluble PEG-based moiety comprising at least 40% PEG;
—$R^2$, —$R^3$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—$R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —C(O)N($R^7$)—, —O—, —S— and —N($R^7$)—;
—Nu is a nucleophile selected from the group consisting of —N($R^7R^{7a}$), —N($R^7$OH), —N($R^7$)—N($R^{7a}R^{7b}$), —S($R^7$), —COOH,

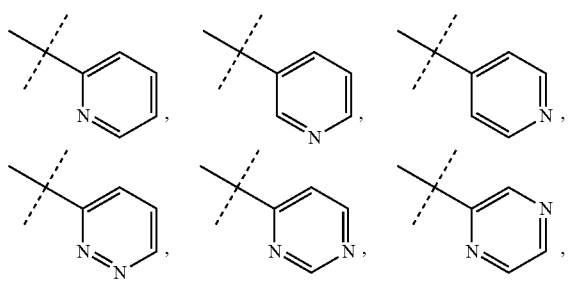

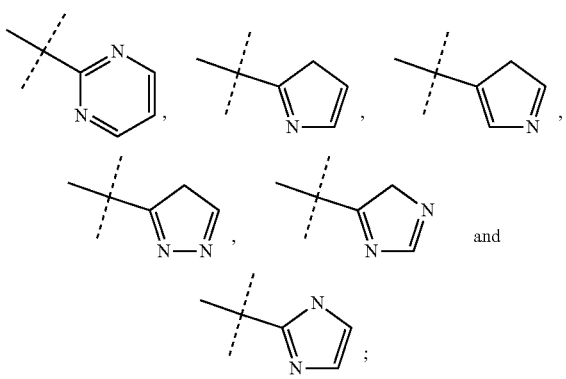

—Ar— is selected from the group consisting of

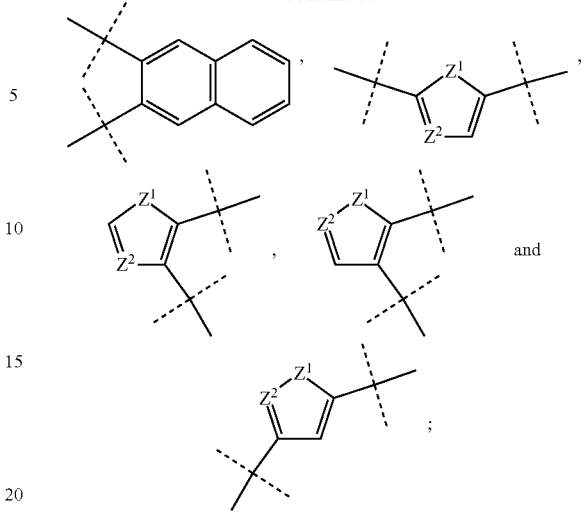

wherein
dashed lines indicate attachment to the rest of the prodrug,
—$Z^1$— is selected from the group consisting of —O—, —S— and —N($R^7$)—, and
—$Z^2$— is —N($R^7$)—; and
—$R^7$, —$R^{7a}$, —$R^{7b}$ are independently of each other selected from the group consisting of —H, $C_{1-6}$ alkyl, $C_{2-6}$ alkenyl and $C_{2-6}$ alkynyl;
wherein the prodrug of formula (Ia) and (Ib) is optionally further substituted.

In certain embodiments the long-acting hGH is of formula (Ia). In certain embodiments the long-acting hGH is of formula (Ib).

In a preferred embodiment =$Y^1$ of formula (Ia) and (Ib) is =O.

In a preferred embodiment —$Y^2$— of formula (Ia) and (Ib) is —O—.

In a preferred embodiment —$Y^3$— of formula (Ia) and (Ib) is —O—.

In a preferred embodiment —$Y^4$— of formula (Ia) and (Ib) is —$NR^5$—.

In a preferred embodiment =$Y^5$ of formula (Ia) and (Ib) is =O.

In a preferred embodiment n of formula (Ia) and (Ib) is 0 or 1. Most preferably, n of formula (Ia) and (Ib) is 0.

Preferably, $R^1$ of formula (Ia) and (Ib) has a molecular weight ranging from 10 to 250 kDa, even more preferably from 15 to 150 kDa.

In one particularly preferred embodiment $R^1$ of formula (Ia) and (Ib) has a molecular weight ranging from 30 to 50 kDa, even more preferably from 35 to 45 kDa, even more preferably from 38 to 42 kDa and most preferably has a molecular weight of about 40 kDa.

In another equally preferred embodiment $R^1$ of formula (Ia) and (Ib) has a molecular weight ranging from 60 to 100 kDa, even more preferably from 70 to 90 kDa, even more preferably from 75 to 85 kDa and most preferably has a molecular weight of about 80 kDa.

Preferably, $R^1$ of formula (Ia) and (Ib) is branched and comprises at least three polymeric moieties.

More preferably, $R^1$ of formula (Ia) and (Ib) comprises at least one branching point, preferably at least two branching points, and at least three polymeric chains which polymeric chains are preferably PEG-based, wherein each branching point is preferably selected from the group consisting of —N<, —CR$^8$< and >C<, wherein R$^8$ is selected from the group consisting of —H, C$_{1-6}$ alkyl, C$_{2-6}$ alkenyl and C$_{2-6}$ alkynyl; wherein C$_{1-6}$ alkyl, C$_{2-6}$ alkenyl and C$_{2-6}$ alkynyl are optionally substituted with one or more R$^9$, which are the same or different, and wherein C$_{1-6}$ alkyl, C$_{2-6}$ alkenyl and C$_{2-6}$ alkynyl are optionally interrupted with —C(O)O—, —O—, —C(O)—, —C(O)N(R$^{10}$)—, —S(O)$_2$N(R$^{10}$)—, —S(O)N(R$^{10}$)—, —S(O)$_2$—, —S(O)—, —N(R$^{10}$)S(O)$_2$N(R$^{10a}$)—, —S—, —N(R$^{10}$)—, —OC(OR$^{10}$)(R$^{10a}$)—, —N(R$^{10}$)C(O)N(R$^{10a}$)—, and —OC(O)N(R$^{10}$)—; wherein R$^9$, R$^{10}$ and R$^{10a}$ are selected from —H, C$_{1-6}$ alkyl, C$_{2-6}$ alkenyl and C$_{2-6}$ alkynyl.

In one preferred embodiment R$^1$ of formula (Ia) and (Ib) comprises a first branching point BP$^1$ from which at least two moieties C$^1$ and C$^2$ extend of which at least one comprises an at least second branching point BP$^2$ from which at least two moieties P$^1$ and P$^2$ extend. More preferably, R$^1$ comprises a first branching point BP$^1$ from which two moieties C$^1$ and C$^2$ extend, which moiety C$^1$ comprises a branching point BP$^2$ from which at least two moieties P$^1$ and P$^2$ extend, and which moiety C$^2$ comprises a third branching point BP$^3$ from which at least two moieties P$^3$ and P$^4$ extend.

In another preferred embodiment R$^1$ comprises a moiety C$^1$ which comprises a first branching point BP$^1$, a second branching point BP$^2$ and a third branching point BP$^3$, wherein at least one moiety P$^1$ extends from BP$^1$, at least one moiety P$^2$ extends from BP$^2$ and at least one moiety P$^3$ extends from BP$^3$. More preferably, R$^1$ comprises a moiety C$^1$ which comprises a first branching point BP$^1$, a second branching point BP$^2$, a third branching point BP$^3$ and a forth branching point BP$^4$, wherein at least a moiety P$^1$ extends from BP$^1$, at least a moiety P$^2$ extends from BP$^2$, at least a moiety P$^3$ extends from BP$^3$ and at least a moiety P$^4$ extends from BP$^4$.

Preferably, BP$^1$, BP$^2$, BP$^3$ and BP$^4$ are independently of each other selected from —CR$^8$<, >C< and —N<, wherein R$^8$ is selected from —H, C$_{1-6}$ alkyl, C$_{2-6}$ alkenyl and C$_{2-6}$ alkynyl; wherein C$_{1-6}$ alkyl, C$_{2-6}$ alkenyl and C$_{2-6}$ alkynyl are optionally substituted with one or more R$^9$, which are the same or different, and wherein C$_{1-6}$ alkyl, C$_{2-6}$ alkenyl and C$_{2-6}$ alkynyl are optionally interrupted with —C(O)O—, —O—, —C(O)—, —C(O)N(R$^{10}$)—, —S(O)$_2$N(R$^{10}$)—, —S(O)N(R$^{10}$)—, —S(O)$_2$—, —S(O)—, —N(R$^{10}$)S(O)$_2$N(R$^{10a}$)—, —S—, —N(R$^{10}$)—, —OC(OR$^{10}$)(R$^{10a}$)—, —N(R$^{10}$)C(O)N(R$^{10a}$) and —OC(O)N(R$^{10}$)—; wherein R$^9$, R$^{10}$ and R$^{10a}$ are selected from —H, C$_{1-6}$ alkyl, C$_{2-6}$ alkenyl and C$_{2-6}$ alkynyl.

Preferably, C$^1$ and C$^2$ are independently of other selected from C$_{1-50}$ alkyl, C$_{2-50}$ alkenyl and C$_{2-50}$ alkynyl; wherein C$_{1-50}$ alkyl, C$_{2-50}$ alkenyl and C$_{2-50}$ alkynyl are optionally substituted with one or more R$^{11}$, which are the same or different, and wherein C$_{1-50}$ alkyl, C$_{2-50}$ alkenyl and C$_{2-50}$ alkynyl are optionally interrupted with one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

wherein -T- is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, and wherein each -T- is independently optionally substituted with one or more R$^{11}$, which are the same or different;

wherein each R$^{11}$ is independently selected from the group consisting of halogen, —CN, oxo (=O), —COOR$^{12}$, —OR$^{12}$, —C(O)R$^{12}$, —C(O)N(R$^{12}$R$^{12a}$), —S(O)$_2$N(R$^{12}$R$^{12a}$), —S(O)N(R$^{12}$R$^{12a}$), —S(O)$_2$R$^{12}$, —S(O)R$^{12}$, —N(R$^{12}$)S(O)$_2$N(R$^{12a}$R$^{12b}$), —SR$^{12}$, —N(R$^{12}$R$^{12a}$), —NO$_2$, —OC(O)R$^{12}$, —N(R$^{12}$)C(O)R$^{12a}$, —N(R$^{12}$)S(O)$_2$R$^{12a}$, —N(R$^{12}$)S(O)R$^{12a}$, —N(R$^{12}$)C(O)OR$^{12a}$, —N(R$^{12}$)C(O)N(R$^{12a}$R$^{12b}$), —OC(O)N(R$^{12}$R$^{12a}$), and C$_{1-6}$ alkyl; wherein C$_{1-6}$ alkyl is optionally substituted with one or more halogen, which are the same or different;

and wherein each R$^{12}$, R$^{12a}$ and R$^{12b}$ are independently of each other selected from the group consisting of —H, C$_{1-6}$ alkyl, C$_{2-6}$ alkenyl and C$_{2-6}$ alkynyl, wherein C$_{1-6}$ alkyl, C$_{2-6}$ alkenyl and C$_{2-6}$ alkynyl is optionally substituted with one or more halogen, which are the same or different.

Preferably, P$^1$, P$^2$, P$^3$, P$^4$ are independently of each other a polymeric moiety, more preferably a PEG-based chain comprising at least 40% PEG, even more preferably at least 50% PEG, even more preferably at least 60% PEG, even more preferably at least 70% PEG, even more preferably at least 80% PEG, even more preferably at least 90% PEG and most preferably at least 95% PEG.

In one preferred embodiment P$^1$, P$^2$, P$^3$ and P$^4$ have independently of each other a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment P$^1$, P$^2$, P$^3$ and P$^4$ have independently of each other a molecular weight ranging from 10 to 30 kDa, more preferably ranging from 15 to 25 kDa, even more preferably ranging from 17 to 23 kDa and most preferably have a molecular weight of about 20 kDa.

In a preferred embodiment —R$^1$ of formula (Ia) and (Ib) comprises a moiety of formula (II)

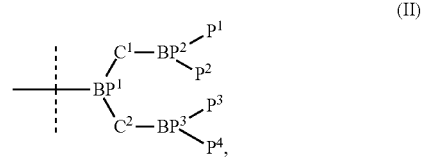

(II)

wherein
—BP<, —BP$^2$<, —BP$^3$< are independently of each other selected from the group consisting of —N< and —C(R$^8$<
R$^8$ is selected from the group consisting of H, C$_{1-6}$ alkyl, C$_{2-6}$ alkenyl and C$_{2-6}$ alkynyl;
—P$^1$, —P$^2$, —P$^3$, —P$^4$ are independently of each other a PEG-based chain comprising at least 400% PEG and having a molecular weight ranging from 5 to 30 kDa;
—C$^1$—, —C$^2$— are independently of each other selected from the group consisting of C$_{1-50}$ alkyl, C$_{2-50}$ alkenyl, and C$_{2-50}$ alkynyl; wherein C$_{1-50}$ alkyl, C$_{2-50}$ alkenyl, and C$_{2-50}$ alkynyl are optionally substituted with one or more R$^9$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{10}$)—, —S(O)$_2$N(R$^{10}$)—, —S(O)N(R$^{10}$)—, —N(R$^{10}$)—, —OC(OR$^{10}$)(R$^{10a}$)—, —N(R$^{10}$)C(O)N(R$^{10a}$)—, and —OC(O)N(R$^{10}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more R$^9$, which are the same or different;

each R$^9$ is independently selected from the group consisting of halogen, —CN, oxo (=O), —COOR$^{11}$, —OR$^{11}$, —C(O)R$^{11}$, —C(O)N(R$^{11}$R$^{11a}$), —S(O)$_2$N(R$^{11}$R$^{11a}$), —S(O)N(R$^{11}$R$^{11a}$), —S(O)$_2$R$^{11}$, —S(O)R$^{11}$, —N(R$^{11}$)S(O)$_2$N(R$^{11a}$R$^{11b}$), —SR$^{11}$, —N(R$^{11}$R$^{11a}$), —NO$_2$, —OC(O)R$^{11}$, —N(R$^{11}$)C(O)R$^{11a}$, —N(R$^{11}$)S(O)$_2$R$^{11a}$, —N(R$^{11}$)S(O)R$^{11a}$, —N(R$^{11}$)C(O)OR$^{11a}$, —N(R$^{11}$)C(O)N(R$^{11a}$R$^{11b}$), —OC(O)N(R$^{11}$R$^{11a}$), and C$_{1-6}$ alkyl; wherein C$_{1-6}$ alkyl is optionally substituted with one or more halogen, which are the same or different; and each R$^{10}$, R$^{10a}$, R$^{11}$, R$^{11a}$ and R$^{11b}$ is independently selected from the group consisting of —H, and C$_{1-6}$ alkyl, wherein C$_{1-6}$ alkyl is optionally substituted with one or more halogen, which are the same or different.

In a preferred embodiment BP$^1$ of formula (II) is —N<.

In a preferred embodiment BP$^2$ and BP$^2$ of formula (II) are both —CH<.

It is advantageous if the first branching point BP$^1$ and the attachment site of X are separated by no more than a certain number of atoms.

Preferably, the critical distance in the prodrugs of formula (Ia) and (Ib) is less than 60 atoms, more preferably less than 50 atoms, even more preferably less than 40 atoms, even more preferably less than 30 atoms, even more preferably less than 20 atoms and most preferably less than 10 atoms.

The term "critical distance" refers to the shortest distance measured as the number of atoms between the first branching point BP$^1$ comprised in R$^1$ and the atom marked with the asterisk in formula (a), if the prodrug is of formula (Ia), or refers to the number of atoms between the first branching point BP$^1$ comprised in R$^1$ and the atom marked with the asterisk in formula (b), if the prodrug is of formula (Ib):

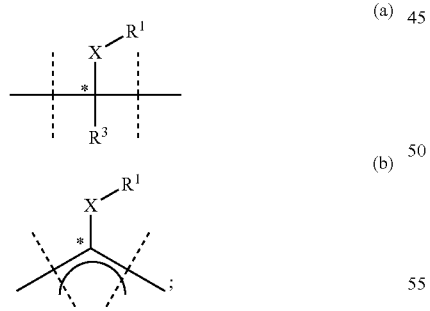

wherein the dashed lines indicate attachment to the remainder of the prodrug of formula (Ia) in the case of (a) and to the remainder of the prodrug of formula (Ib) in the case of (b).

In a preferred embodiment —P$^1$, —P$^2$, —P$^3$, —P$^4$ of formula (II) independently of each other have a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment —P$^1$, —P$^2$, —P$^3$, —P$^4$ of formula (II) independently of each other have a molecular weight ranging from 10 to 30 kDa, more preferably ranging from 15 to 25 kDa, even more preferably ranging from 17 to 23 kDa and most preferably have a molecular weight of about 20 kDa.

In a preferred embodiment C$^1$ and C$^2$ of formula (II) are C$_{1-50}$ alkyl interrupted by one or more of the groups selected from the group consisting of —O—, —C(O)N(R$^{10}$)— and 3- to 10 membered heterocyclyl; wherein the 3- to 10 membered heterocyclyl is substituted with at least one oxo (=O).

Most preferably, C$^1$ and C$^2$ of formula (II) are of formula (IIa)

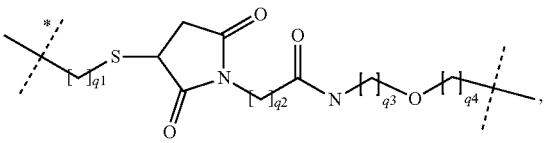

wherein the dashed line marked with the asterisk indicates attachment to BP$^1$;

the unmarked dashed line indicates attachment to BP$^2$ or BP$^3$, respectively;

q1 is 1, 2, 3, 4, 5, 6, 7 or 8; preferably q1 is 4, 5, 6, 7, or 8; more preferably q1 is 5, 6 or 7; most preferably q1 is 6;

q2 is 1, 2, 3, 4, or 5; preferably q2 is 1, 2 or 3; most preferably q2 is 2;

q3 is 1, 2, 3, 4, 5, 6, 7 or 8; preferably q3 is 2, 3, 4, or 5; more preferably q3 is 2, 3 or 4; most preferably q3 is 3;

q4 is 1, 2 or 3; most preferably, q4 is 1.

In a preferred embodiment P$^1$, P$^2$, P$^3$ and P$^4$ of formula (II) are independently of each other of formula (IIb)

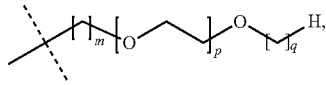

wherein the dashed line indicates attachment the remainder of R$^1$, i.e. to BP$^2$ or BP$^3$, respectively, m is 0 or 1, p is an integer ranging from 57 to 1420, more preferably 85 to 850; and q is selected from the group consisting of 1, 2, 3, 4, 5, and 6.

In a preferred embodiment p of formula (IIb) ranges from 170 to 284, even more preferably from 198 to 255 and most preferably from 215 to 238.

In an equally preferred embodiment p of formula (IIb) ranges from 340 to 568, even more preferably from 398 to 510 and most preferably from 426 to 482.

More preferably, —R¹ comprises a moiety of formula (IIc):

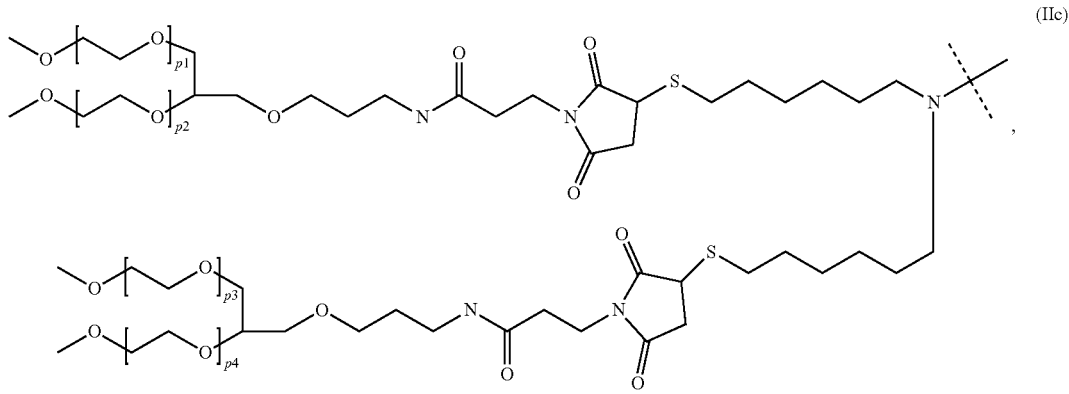

wherein
p1, p2, p3, p4 are independently an integer ranging from 57 to 1420, even more preferably from 85 to 850.

In a preferred embodiment p1, p2, p3 and p4 of formula (IIc) are an integer independently selected from 170 to 284, even more preferably from 198 to 255 and most preferably from 215 to 238.

In an equally preferred embodiment p1, p2, p3 and p4 of formula (IIc) are an integer independently selected from 340 to 568, even more preferably from 398 to 510 and most preferably from 426 to 482.

In a preferred embodiment —R² of formula (Ib) is selected from the group consisting of —H, methyl, ethyl, n-propyl, isopropyl, n-butyl, isobutyl, sec-butyl and tert-butyl. More preferably, —R² of formula (Ib) is selected from the group consisting of —H, methyl, ethyl, n-propyl and isopropyl. Even more preferably —R² of formula (Ib) is selected from —H, methyl and ethyl. Most preferably, —R² of formula (Ib) is —H.

In a preferred embodiment —R³ of formula (Ia) and (Ib) is selected from the group consisting of —H, methyl, ethyl, n-propyl, isopropyl, n-butyl, isobutyl, sec-butyl and tert-butyl. More preferably, —R³ of formula (Ia) and (Ib) is selected from the group consisting of —H, methyl, ethyl, n-propyl and isopropyl. Even more preferably —R³ of formula (Ia) and (Ib) is selected from —H, methyl and ethyl. Most preferably, —R³ of formula (Ia) and (Ib) is —H.

In a preferred embodiment, each —R⁴ of formula (Ia) and (Ib) is independently selected from methyl, ethyl, n-propyl, isopropyl, n-butyl, isobutyl, sec-butyl and tert-butyl. More preferably, —R⁴ of formula (Ia) and (Ib) is selected from the group consisting of methyl, ethyl, n-propyl and isopropyl. Even more preferably —R⁴ of formula (Ia) and (Ib) is selected from methyl and ethyl.

In a preferred embodiment —R⁵ of formula (Ia) and (Ib) is selected from the group consisting of —H, methyl, ethyl, n-propyl, isopropyl, n-butyl, isobutyl, sec-butyl and tert-butyl. More preferably, —R⁵ of formula (Ia) and (Ib) is selected from the group consisting of —H, methyl, ethyl, n-propyl and isopropyl. Even more preferably —R⁵ of formula (Ia) and (Ib) is selected from methyl and ethyl. Most preferably, —R⁵ of formula (Ia) and (Ib) is methyl.

In a preferred embodiment —R⁶ and —R⁶ᵃ of formula (Ia) and (Ib) are independently selected from the group consisting of —H, methyl, ethyl, n-propyl, isopropyl, n-butyl, isobutyl, sec-butyl and tert-butyl. More preferably, —R⁶ and —R⁶ᵃ of formula (Ia) and (Ib) are independently selected from the group consisting of —H, methyl, ethyl, n-propyl and isopropyl. Even more preferably —R⁶ and —R⁶ᵃ of formula (Ia) and (Ib) are independently selected from —H, methyl and ethyl. Most preferably, —R⁶ and —R⁶ᵃ of formula (Ia) and (Ib) are both —H.

In a preferred embodiment X of formula (Ia) and (Ib) is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1a}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COOR$^{z5}$, —OR$^{z5}$, —C(O)R$^{z5}$, —C(O)N(R$^{z5}$R$^{z5a}$), —S(O)$_2$N(R$^{z5}$R$^{z5a}$), —S(O)N(R$^{z5}$R$^{z5a}$), —S(O)$_2$R$^{z5}$, —S(O)R$^{z5}$, —N(R$^{z5}$)S(O)$_2$N(R$^{z5a}$R$^{z5b}$), —SR$^{z5}$, —N(R$^{z5}$R$^{z5a}$), —NO$_2$, —OC(O)R$^{z5}$, —N(R$^{z5}$)C(O)R$^{z5a}$, —N(R$^{z5}$)S(O)$_2$R$^{z5a}$, —N(R$^{z5}$)S(O)R$^{z5a}$, —N(R$^{z5}$)C(O)OR$^{z5a}$, —N(R$^{z5}$)C(O)N(R$^{z5a}$R$^{z5b}$), —OC(O)N(R$^{z5}$R$^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, X of formula (Ia) and (Ib) is selected from the group consisting of $C_{1-10}$ alkyl, $C_{2-10}$ alkenyl, and $C_{2-10}$ alkynyl; wherein $C_{1-10}$ alkyl, $C_{2-10}$ alkenyl, and $C_{2-10}$ alkynyl are optionally substituted with one or more $R^{z2}$, which are the same or different and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —S—, —N(R$^{z3}$)—, —OC(OR$^{z3}$)(R$^{z3a}$)—, —N(R$^{z3}$)C(O)N(R$^{z3a}$)—, and —OC(O)N(R$^{z3}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from $C_{1-6}$ alkyl, wherein $C_{1-6}$ alkyl is optionally substituted with one or more halogen, which are the same or different; each $R^{z3}$, $R^{z3a}$ is independently selected from the group consisting of —H, and $C_{1-6}$ alkyl, wherein $C_{1-6}$ alkyl is optionally substituted with one or more halogen, which are the same or different.

Even more preferably, X of formula (Ia) and (Ib) is $C_{1-10}$ alkyl which is optionally interrupted by one or more groups selected from the group consisting of —C(O)O—, —O—, —C(O)—, —C(O)N(R$^3$)—, —S—, —N(R$^{z3}$)—, —OC(OR$^{z3}$)(R$^{z3a}$)— and —OC(O)N(R$^{z3}$)—; wherein $R^{z3}$ and $R^{z3a}$ are independently selected from —H and $C_{1-6}$ alkyl.

Most preferably, X of formula (Ia) and (Ib) is of formula (III)

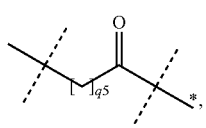

(III)

wherein the dashed line marked with the asterisk indicates attachment to the $R^1$;

the unmarked dashed line indicates attachment to remainder of the prodrug;

q5 is 1, 2, 3, 4, 5, 6, 7 or 8; preferably q5 is 1, 2, 3, 4, or 5; more preferably q5 is 2, 3 or 4; most preferably q5 is 3;

Preferably, Ar of formula (Ia) and (Ib) is phenyl. Most preferably Ar of formula (Ia) and (Ib) is

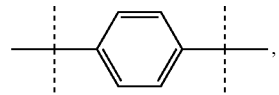

wherein the dashed lines indicate attachment to the remainder of the prodrug of formula (Ia) or (Ib).

Preferably W of formula (Ia) and (Ib) is $C_{1-20}$ alkyl, optionally interrupted with $C_{3-10}$ cycloalkyl, —C(O)—, —C(O)N(R$^7$)—, —O—, —S— and —N(R$^7$)—. Even more preferably, W of formula (Ia) and (Ib) is $C_{1-10}$ alkyl, optionally interrupted with $C_{3-10}$ cycloalkyl, —C(O)—, —C(O)N(R$^7$)—, —O—, —S— and —N(R$^7$)—. Even more preferably, W of formula (Ia) and (Ib) is $C_{1-6}$ alkyl, optionally interrupted with $C_{3-10}$ cycloalkyl, —C(O)—, —C(O)N(R$^7$)—, —O—, —S— and —N(R$^7$)—. Most preferably, W of formula (Ia) and (Ib) is

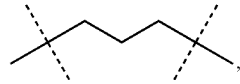

wherein the dashed lines indicate attachment to the rest of the molecule.

Preferably, —Nu of formula (Ia) and (Ib) is —N(R$^7$R$^{7a}$).

Preferably, —R$^7$ and —R$^{7a}$ of formula (Ia) and (Ib) are independently of each other selected from the group consisting of —H, methyl, ethyl, n-propyl, isopropyl, n-butyl, isobutyl, sec-butyl and tert-butyl. More preferably, —R$^7$ and —R$^{7a}$ of formula (Ia) and (Ib) are independently of each other selected from —H, methyl, ethyl, n-propyl and isopropyl. Even more preferably, —R$^7$ and —R$^{7a}$ of formula (Ia) and (Ib) are independently of each other selected from methyl or ethyl. Most preferably, —R$^7$ and —R$^{7a}$ of formula (Ia) and (Ib) are both methyl.

Most preferably, the long-acting growth hormone is a polymeric hGH prodrug of formula (IV)

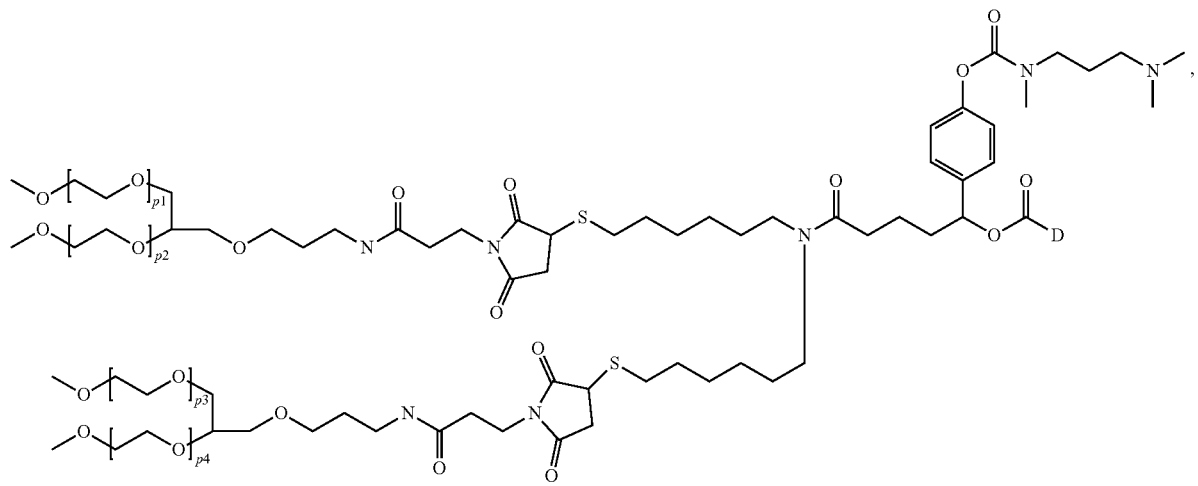

(IV)

wherein

D is a hGH moiety connected to the rest of the molecule through an amine functional group; and p1, p2, p3, p4 are independently an integer ranging from 57 to 1420, even more preferably from 85 to 850.

In a preferred embodiment p1, p2, p3 and p4 of formula (IV) are an integer independently selected from 170 to 284, even more preferably from 198 to 255 and most preferably from 215 to 238.

In an equally preferred embodiment p1, p2, p3 and p4 of formula (IV) are an integer independently selected from 340 to 568, even more preferably from 398 to 510 and most preferably from 426 to 482.

Preferably, the long-acting growth hormone formulation comprises at least one long-acting growth hormone selected from the group consisting of ACP-001, ACP-011, VRS-317, MOD-4023, somatrogon, hGH-CTP, albutropin, ARX201, ALTU-238, PHA-794428, hGH-OctoDex, NNC126-0083, somapacitan, somavaratan, Nutropin Depot, LB03002, Somatropin Biopartners, LAPS-hGH, NNC0195-0092, Hytropin, GX-H9, Jintrolong, and TV-1106.

In certain embodiments the long-acting growth hormone is ACP-001. ACP-001 has the structure of formula (IV), in which p1, p2, p3 and p4 range from 398 to 510, meaning that the molecular weight of the four PEG moieties is about 80 kDa.

In certain embodiments the long-acting growth hormone is ACP-011. ACP-011 has the structure of formula (IV), in which p1, p2, p3 and p4 range from 198 to 255, meaning that the molecular weight of the four PEG moieties is about 40 kDa.

In certain embodiments the long-acting growth hormone is somapacitan. Somapacitan has the following structure:

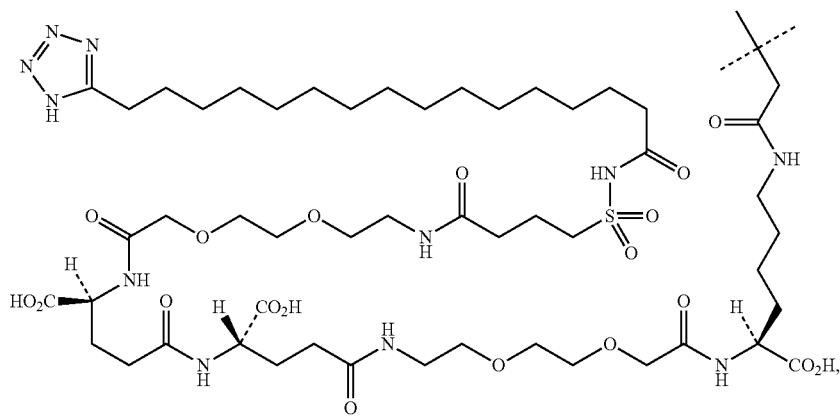

wherein the dashed line indicates attachment to the sulfur of the cysteine at position 101 of SEQ ID NO:2, which is

```
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

CVYGASDSNVYDLLKDLEEGIQTLMGRLEDGSPRTGQIFKQTYSKFDTN

SHNDDALLKNYGLLYCFRKDMDKVETFLRIVQCRSVEGSCGF
```

SEQ ID NO:2 corresponds to SEQ ID NO:1, in which the leucine at position 101 is replaced by cysteine.

In one embodiment the pharmaceutical composition comprising the long-acting growth hormone is a liquid formulation.

In another embodiment the pharmaceutical composition comprising the long-acting growth hormone is a dry formulation.

In a preferred embodiment the pharmaceutical composition comprising the long-acting growth hormone is stable for at least 3 months at refrigerated temperature, i.e. at 2 to 8° C.

In another preferred embodiment the pharmaceutical composition comprising the long-acting growth hormone is stable for at least 3 months at room temperature, i.e. at 18 to 30° C.

In another preferred embodiment, the long-acting growth hormone is administered in combination with a C-type Natriuretic Peptide agonist.

In another preferred embodiment, the long-acting growth hormone is administered in combination with a soluble FGFR3.

Such liquid or dry pharmaceutical composition comprising the long-acting growth hormone comprises one or more excipients. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. The pharmaceutical composition comprising the long-acting growth hormone preferably comprises one or more excipients selected from the group consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral formulations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilisation is achieved by strengthening of the protein-stabilising forces, by destabilisation of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used.

(v) Anti-adsorption agents: Mainly ionic or non-ionic surfactants or other proteins or soluble polymers are used to coat or adsorb competitively to the inner surface of the formulation's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value.

(vi) Oxidation protection agents: antioxidants such as ascorbic acid, ectoine, methionine, glutathione, monothioglycerol, morin, polyethylenimine (PEI), propyl gallate, and vitamin E. Chelating agents such as citric acid, EDTA, hexaphosphate, and thioglycolic acid may also be used.

(vii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

Another aspect of the present invention is a method of treating a patient suffering from a growth disorder, wherein the method comprising the step of administering an effective amount of the long-acting growth hormone formulation of the present invention to the patient.

Said administration of the long-acting growth hormone leads to superior efficacy compared to equimolar administration of a daily somatropin.

In certain embodiments said superior efficacy is measured as annualized height velocity.

Another aspect of the present invention is a method of treating growth hormone deficiency, wherein the method comprises the step of administering a long-acting growth hormone formulation to patients with growth hormone deficiency and wherein the administration of the long-acting growth hormone leads to a reduction in non-responders compared to administration of an equimolar dose of a daily somatropin.

Preferably, the long-acting growth hormone formulation is administered to a patient with a time period of at least two days between two administrations. More preferably, the time period between two administrations is at least 3 days, even more preferably at least 4 days, even more preferably at least 5 days, even more preferably at least 6 days and most preferably the time period between two administrations is 7 days. In another embodiment the time period between two administrations is 14 days or one month.

Preferably, the growth hormone deficiency is treated for a time period of at least 6 months, such as of at least 8 months, such as of at least 10 months, such as of at least 12 months, such as of at least 14 months, such as of at least 16 months, such as of at least 20 months, such as of at least 24 months, such as of at least 30 months or such as of at least 36 months.

Another aspect of the present invention is a method of administering the long-acting growth hormone formulation to patients with growth hormone deficiency and wherein the administration of the long-acting growth hormone leads to superior efficacy compared to administration of an equimolar dose of a daily somatropin.

As used herein, the term "growth hormone deficiency" relates to any disease which benefits from the administration of growth hormone. Preferably, growth hormone deficiency is selected from the group consisting of growth hormone deficiency (GHD) in children, idiopathic short stature (ISS), short stature homeobox (SHOX) gene mutations, Turner syndrome (TS), Noonan syndrome (NS), Prader-Willi syndrome (PWS), children born small for gestational age (SGA), chronic renal insufficiency (CRI), growth hormone deficiency (GHD) in adults, wasting due to HIV or AIDS or other malignancies, short bowel syndrome (SBS), sarcopenia, and frailty.

In another embodiment the growth hormone deficiency is GHD in adults. In another embodiment the growth hormone deficiency is ISS. In another embodiment the growth hormone deficiency are SHOX gene mutations. In another embodiment the growth hormone deficiency is TS. In another embodiment the growth hormone deficiency is NS. In another embodiment the growth hormone deficiency is PWS. In another embodiment the growth hormone deficiency is SGA. In another embodiment the growth hormone deficiency is CRI.

In another embodiment the growth hormone deficiency is wasting due to HIV or AIDS or other malignancies. In another embodiment the growth hormone deficiency is SBS. In another embodiment the growth hormone deficiency is sarcopenia. In another embodiment the growth hormone deficiency is frailty. In a preferred embodiment the growth hormone deficiency is GHD in children.

EXAMPLES

Methods

Cation Exchange Chromatography

The purification of conjugates by cation exchange chromatography was performed using an AKTA Pure system (GE Healthcare) equipped with a Macrocap SP column with a column volume of 279 mL. The respective reaction mixture was applied to the column which was pre-equilibrated in 20 mM sodium acetate, 10 mM L-methionine buffer, pH 4.0 (buffer A). After loading, the column was washed with three column volumes of buffer A to remove any unreacted PEG reagent. Mono-Conjugates were eluted using a gradient of 0-30% buffer B (20 mM sodium acetate, 1 M sodium chloride, pH 4.5) over 15 column volumes. A gradient of 30-80% B over three column volumes was used to elute unreacted growth hormone. The column was cleaned with 3 column volumes of 100% buffer B. The flow rate was 20 mL/min for loading and 25 mL/min during the elution. The elution was monitored by detection at 280 nm.

Height and Height Velocity Measurements

Height measurements were performed using a calibrated wall-mounted (e.g. Harpenden or similar) stadiometer. The results were derived as an arithmetic mean from three separate measurements at each visit. The time of measurement and the auxologist's name, as well as the result were recorded. The calculation of height velocity was performed centrally.

Example 1: Synthesis of Transient 4×10 kDa mPEG-Linker-hGH Monoconjugate 1

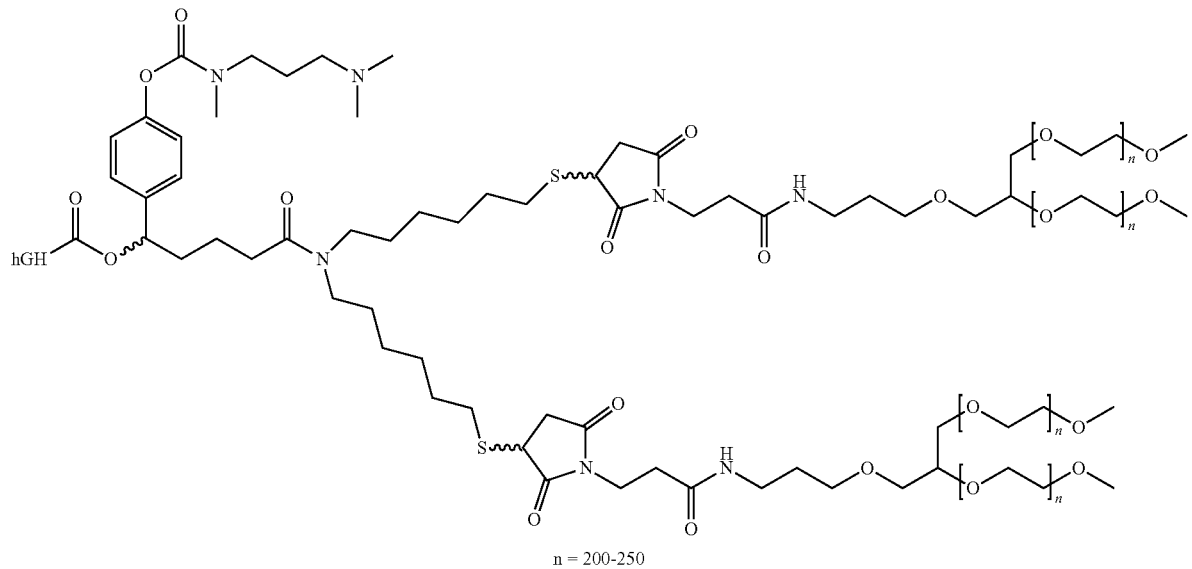

n = 200-250

4×10 kDa mPEG-linker-hGH monoconjugate 1 was synthesized according to a similar procedure as described in WO2009/133137 A2; in detail the manufacturing process was conducted as follows:

hGH was buffer exchanged to 100 mM sodium borate pH 9 and the concentration of hGH was adjusted to 10 mg/mL. A molar excess of 4-arm branched 40 kDa mPEG-pentafluorophenylcarbonate derivative relative to the amount of hGH was dissolved in water to form a 6% (w/w) reagent solution. The reagent solution was added to the hGH solution in a 1-to-1 ratio (based on weight) and mixed. The reaction mixture was incubated under stirring for 105 min at 12-16° C. and subsequently quenched by adding 4 volumes of a solution comprising 27 mM acetic acid and 12.5 mM L-methionine to 1 volume of the reaction mixture to lower the pH of the solution to 4-4.5. After sterile filtration, the reaction mixture was incubated at room temperature for 16±4 h. 4×10 kDa mPEG-linker-hGH monoconjugate 1 was purified by cation exchange chromatography.

Buffer exchange and adjustment to the desired concentration of 4×10 mPEG-linker-hGH monoconjugate 1 was achieved using a tangential-flow filtration system. Herewith the eluate from the cation exchange chromatography was ultra-filtrated and dia-filtrated to formulation buffer (10 mM succinic acid, 85 g/L trehalose dihydrate, pH 5.0 with 1M Tris-solution). Using the same system the trehalose concentration was lowered to 65 g/L and the concentration of this stock solution adjusted to 105±3 mg/mL of 4×10 kDa mPEG-linker-hGH monoconjugate 1 (corresponding to 35±1 mg hGH eq./mL). The formulations as shown in Table 2 were prepared based on this stock-solution of compound 1 by diluting the stock solution with high strength formulation buffer (10 mM succinic acid, 89 g/L trehalose dihydrate, adjusted to pH 5.0 with 1M Tris-base).

TABLE 1

Formulations of 4x 10 kDa mPEG-linker-hGH monoconjugate 1

| Formulation name: | Concentration of 4x 10 kDa mPEG-linker-hGH monoconjugate 1 formulation [mg/mL] | Concentration of hGH eq. [mg hGH eq./mL] |
| --- | --- | --- |
| 2A | 103.8 | 34.6 |
| 2B | 95.1 | 31.7 |
| 2C | 81.9 | 27.3 |
| 2D | 65.1 | 21.7 |
| 2E | 47.4 | 15.8 |

Example 2: Preparation of a Formulation Comprising 4×10 kDa mPEG-Linker-hGH Monoconjugate 1 for Clinical Studies For the usage as an investigational drug in clinical studies 4×10 kDa mPEG-linker-hGH monoconjugate 1 was transformed into a lyophilized drug product in glass vials and was presented in single-use glass vials as lyophilized powder for reconstitution with sWFI and was formulated at a concentration suitable to deliver clinically relevant dose volumes for pediatric patients (<0.60 mL). It was supplied in two vial configurations: 12.1 mg hGH/vial and 24.2 mg hGH/vial.

TABLE 2

Formulation of 4x 10 kDa mPEG-linker-hGH monoconjugate 1

| Name of ingredient | Quality | Function |
| --- | --- | --- |
| 4x 10 kDa mPEG-linker-hGH monoconjugate 1 | cGMP (Manufacturer specification) | Prodrug form of the active pharmaceutical ingredient (API), hGH |
| Succinic acid | NF | Buffering agent |

TABLE 2-continued

Formulation of 4x 10 kDa mPEG-linker-hGH monoconjugate 1

| Name of ingredient | Quality | Function |
|---|---|---|
| Trehalose Dihydrate | Ph. Eur./USP | Tonicifier/lyoprotectant |
| Tris | Ph. Eur./USP | pH adjustment |

Following reconstitution with water for injection (WFI), 4×10 kDa mPEG-linker-hGH monoconjugate 1 was presented as a single-use, sterile solution for subcutaneous (s.c.) injection.

Example 3: Phase 3 Pediatric Study

The formulation of example 3 comprising 4×10 kDa mPEG-linker-hGH monoconjugate 1 was studied in a Phase 3 pediatric growth hormone deficiency trial. Pediatric patients were enrolled across the North America, Europe and Oceania who meet internationally recognized criteria for GHD, including short stature as measured by height and height velocity, two hGH stimulation tests, a bone age evaluation and IGF-I levels below −1 standard deviation score, or SDS. This phase 3 trial was a multicenter, open-label trial, enrolling approximately 161 treatment-naïve children with GHD who were randomized in a 2:1 ratio to receive either once-weekly 4×10 kDa mPEG-linker-hGH monoconjugate 1 (0.24 mg/kg/week subcutaneously) or daily Genotropin® (34 µg/kg/day or 0.24 mg/kg/week subcutaneously) for 52 weeks. The primary endpoint was annualized HV at 52 weeks. The secondary endpoints consisted of safety and tolerability; annualized HV over 52 weeks; change in height standard deviation score (SDS) over 52 weeks; serum IGF-1 and IGFBP-3 levels and change in corresponding SDS over 52 weeks; and incidence of anti-human growth hormone antibodies, including neutralizing antibodies. Additionally, both arms were analyzed for non-responders.

In conclusion, the randomized, open-label, active-controlled trial demonstrated that 4×10 kDa mPEG-linker-hGH monoconjugate 1 (n=105) met its primary objective of non-inferiority and, additionally, was superior to the daily Genotropin (n=56) on the primary endpoint of annualized height velocity (AHV) at 52 weeks. In the primary analysis of the intent-to-treat population using ANCOVA, 4× 10 kDa mPEG-linker-hGH monoconjugate 1 demonstrated an AHV of 11.2 cm/year compared to 10.3 cm/year for the daily hGH. The treatment difference was 0.86 cm/year with a 95 percent confidence interval of +0.22 to +1.50 cm/year and superiority was demonstrated (p=0.0088).

The AHV was greater for 4×10 kDa mPEG-linker-hGH monoconjugate 1 than for the daily hGH at each visit, with the treatment difference reaching statistical significance from week 26 and continued throughout the trial. Incidence of poor responders (AHV<8.0 cm/year) was 4 percent and 11 percent in the 4×10 kDa mPEG-linker-hGH monoconjugate 1 and daily hGH arms, respectively.

4×10 kDa mPEG-linker-hGH monoconjugate 1 was safe and well-tolerated, with adverse events typical of daily hGH therapy and comparable between arms. In addition, observed peak and trough insulin-like growth factor 1 (IGF-1) SDS were approximately +1.3 and −0.5 over 52 weeks, respectively for 4×10 kDa mPEG-linker-hGH monoconjugate 1 compared to an approximate average IGF-1 SDS of 0.0 for the daily hGH at week 52. Furthermore, observed excursions of IGF-1 SDS>2.0 were uncommon (<10 percent of subjects) and IGF-1 SDS>3.0 were rare (<3 percent of subjects). Two subjects in each treatment arm experienced injection site reactions that were considered adverse events.

Example 4: Phase 2 Pediatric Study Somapacitan (NCT02616562, Novo Nordisk; https://clinicaltrials.gov/ct2/show/NCT02616562)

Somapacitan has the structure as shown elsewhere herein.

Design: The study was a multicenter, randomized, controlled, double-blind (somapacitan doses), phase-2 study with a 26-week main and 26-week extension phase performed at 29 sites in 11 countries. 59 GH treatment-naïve pre-pubertal children with GHD were randomized; 58 completed the trial.

Interventions: Three somapacitan doses (0.04 [n=16], 0.08 [n=15] or 0.16 mg/kg/week [n=14]) and daily GH (0.034 mg/kg/day [n=14]), administered subcutaneously.

Main Outcome Measures: Primary endpoint was HV at week 26. Secondary efficacy endpoints included HV SDS and IGF-I SDS.

Results: At week 26, mean (SD) annualized HV for somapacitan groups was 8.0 (2.0), 10.9 (1.9) and 12.9 (3.5)cm/year, respectively, versus 11.4 (3.3) cm/year for daily GH; estimated treatment difference (somapacitan 0.16 mg/kg/week-daily GH): 1.7 [95% CI—0.2; 3.6] cm/year. HV was sustained at week 52, and significantly greater with somapacitan 0.16 mg/kg/week versus daily GH. Mean (SD) change from baseline in HV SDS at week 52 was 4.72 (2.79), 6.14 (3.36) and 8.60 (3.15) for somapacitan groups, respectively, versus 7.41 (4.08) for daily GH. Model-derived mean (SD) IGF-I SDS for the somapacitan groups was −1.62 (0.86), −1.09 (0.78), and 0.31 (1.06), respectively, versus −0.40 (1.50) observed for daily GH. Safety and tolerability were consistent with the profile of daily GH.

Abbreviations

AHV Annual/Annualized Height Velocity
API active pharmaceutical ingredient
cGMP current good manufacturing practice
GH growth hormone
GHD growth hormone deficiency
hGH human growth hormone
mPEG methoxypoly(ethylene glycol)
PEG poly(ethylene glycol)
Ph. Eur. European Pharmacopeia
USP United States Pharmacopeia
Tris Tris(hydroxymethyl)-aminomethan

The invention claimed is:

1. A method of treating growth hormone deficiency in a patient who is a non-responder to treatment with daily human growth hormone, the method comprising the step of administering a therapeutically effective amount of a long-acting growth hormone or a pharmaceutical formulation comprising such long-acting growth hormone, wherein the patient has previously been treated with daily administration of a human growth hormone of SEQ ID NO: 1 in a dose ranging from 0.17 mg/kg/week to 0.30 mg/kg/week and has an annualized height velocity of less than 8.0 cm per year, wherein the long-acting growth hormone is of formula (Ia) or (Ib)

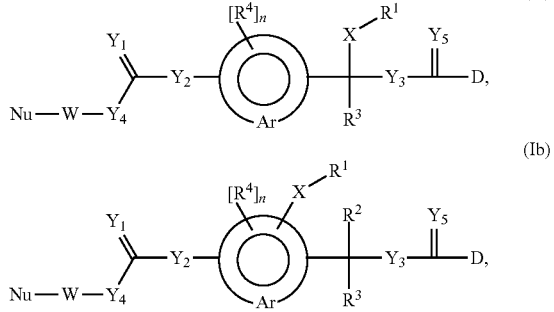

wherein
-D is a hGH moiety connected to the rest of the molecule through an amine functional group;
n is 0, 1, 2, 3, or 4;
—X— is a chemical bond or a spacer;
=$Y_1$, =$Y_5$ are selected independently from the group consisting of =O and =S;
—$Y_2$—, —$Y_3$— are selected from the group consisting of —O— and —S—;
—$Y_4$— is selected from the group consisting of —O—, —$NR^5$— and —$C(R^6R^{6a})$—;
—$R^1$ is a carrier;
—$R^2$, —$R^3$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—$R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —C(O)N($R^7$)—, —O—, —S— and —N($R^7$)—;

-Nu is a nucleophile selected from the group consisting of —N($R^7R^{7a}$), —N($R^7$OH), —N($R^7$)—N($R^{7a}R^{7b}$), —S($R^7$), —COOH,

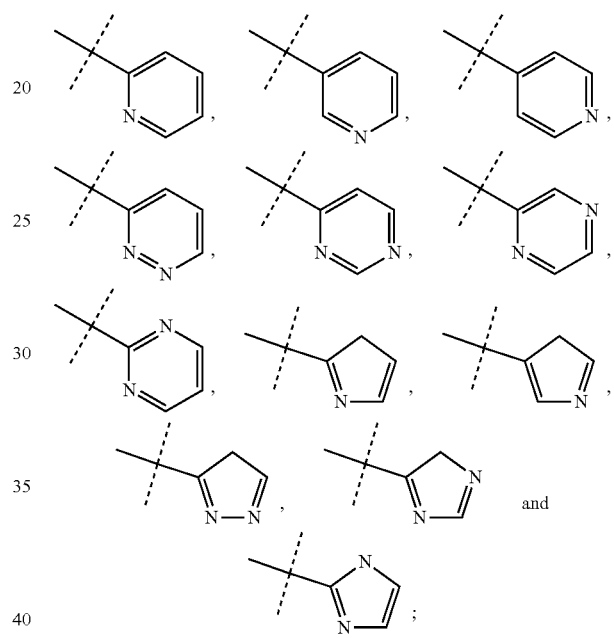

—Ar— is selected from the group consisting of

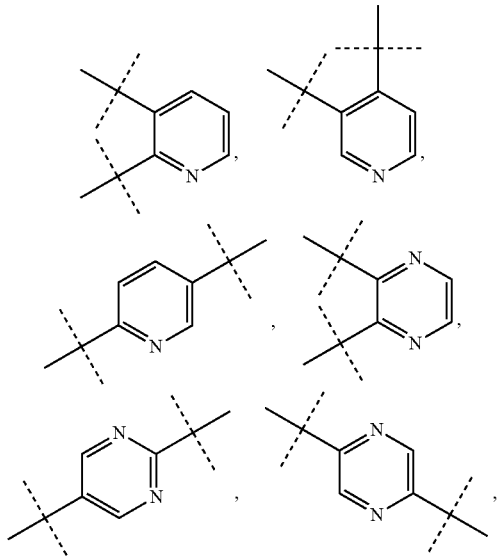

-continued

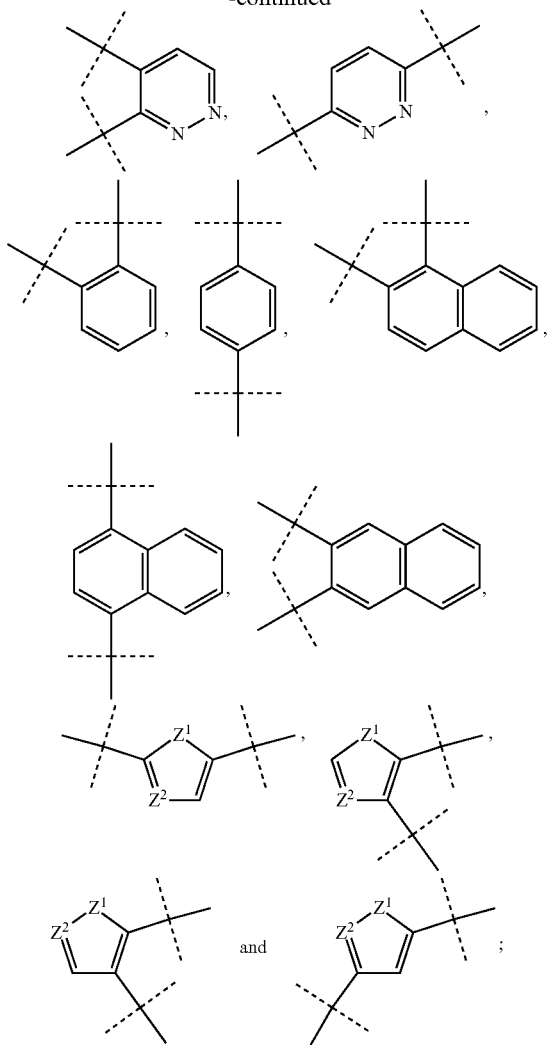

wherein dashed lines indicate attachment to the rest of the long-acting growth hormone, —$Z^1$— is selected from the group consisting of —O—, —S— and —N($R^7$)—, and —$Z^2$— is —N($R^7$)—; and —$R^7$, —$R^{7a}$, —$R^{7b}$ are independently of each other selected from the group consisting of —H, $C_{1-6}$ alkyl, $C_{2-6}$ alkenyl and $C_{2-6}$ alkynyl;

wherein the long-acting growth hormone of formula (Ia) and (Ib) is optionally further substituted.

2. The method of claim 1, wherein the growth hormone deficiency is growth hormone deficiency in children.

3. The method of claim 1, wherein the long acting growth hormone is administered in consecutive administrations 1 week apart.

4. The method of claim 1, wherein the pharmaceutical formulation is a dry formulation.

5. The method of claim 1, wherein the long-acting growth hormone is ACP-011.

6. The method of claim 1, wherein —$R^1$ of formula (Ia) and (Ib) comprises a moiety of formula (II)

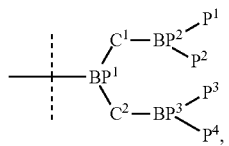

(II)

wherein

—$BP^1$<, —$BP^2$<, —$BP^3$< are independently of each other selected from the group consisting of —N< and —C($R^8$)<;

$R^8$ is selected from the group consisting of H, $C_{1-6}$ alkyl, $C_{2-6}$ alkenyl and $C_{2-6}$ alkynyl;

—$P^1$, —$P^2$, —$P^3$, —$P^4$ are independently of each other a PEG-based chain comprising at least 40% PEG and having a molecular weight ranging from 5 to 30 kDa;

—$C^1$—, —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{10}$)—, —S(O)$_2$N($R^{10}$)—, —S(O) N($R^{10}$)—, —S(O)$_2$—, —S(O)—, —N($R^{10}$)S(O)$_2$N($R^{10a}$)—, —S—, —N($R^{10}$)—, —OC(O$R^{10}$) ($R^{10a}$)—, —N($R^{10}$)C(O)N($R^{10a}$)—, and —OC(O)N($R^{10}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;

each $R^9$ is independently selected from the group consisting of halogen, —CN, oxo (=O), —COO$R^{11}$, —O$R^{11}$, —C(O) $R^{11}$, —C(O)N($R^{11}R^{11a}$), —S(O)$_2$N($R^{11}R^{11a}$), —S(O) N($R^{11}R^{11a}$), —S(O)$_2R^{11}$, —S(O) $R^{11}$, —N($R^{11}$)S(O)$_2$N($R^{11a}R^{11b}$), —S$R^{11}$, —N($R^{11}R^{11a}$), —NO$_2$, —OC(O) $R^{11}$, —N($R^{11}$) C(O) $R^{11a}$, —N($R^{11}$)S(O)$_2R^{11a}$, —N($R^{11}$) S(O) $R^{11a}$, —N($R^{11}$) C(O)O$R^{11a}$, —N($R^{11}$)C(O)N($R^{11a}R^{11b}$), —OC(O)N($R^{11}R^{11a}$), and $C_{1-6}$ alkyl; wherein $C_{1-6}$ alkyl is optionally substituted with one or more halogen, which are the same or different; and each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

7. The method of claim 1, wherein —$R^1$ comprises a moiety of formula (IIc):

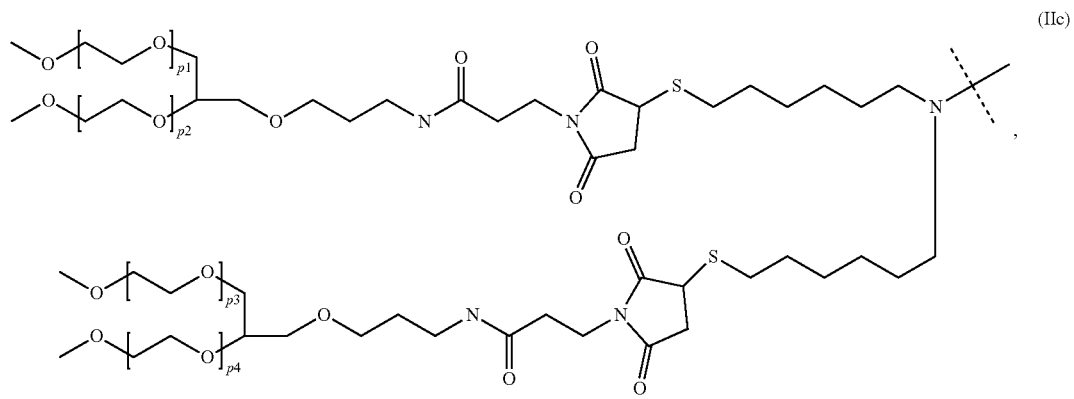

wherein
p1, p2, p3, p4 are independently an integer ranging from 170 to 284.

8. The method of claim 1, wherein the long-acting growth hormone is a polymeric hGH prodrug of formula (IV)

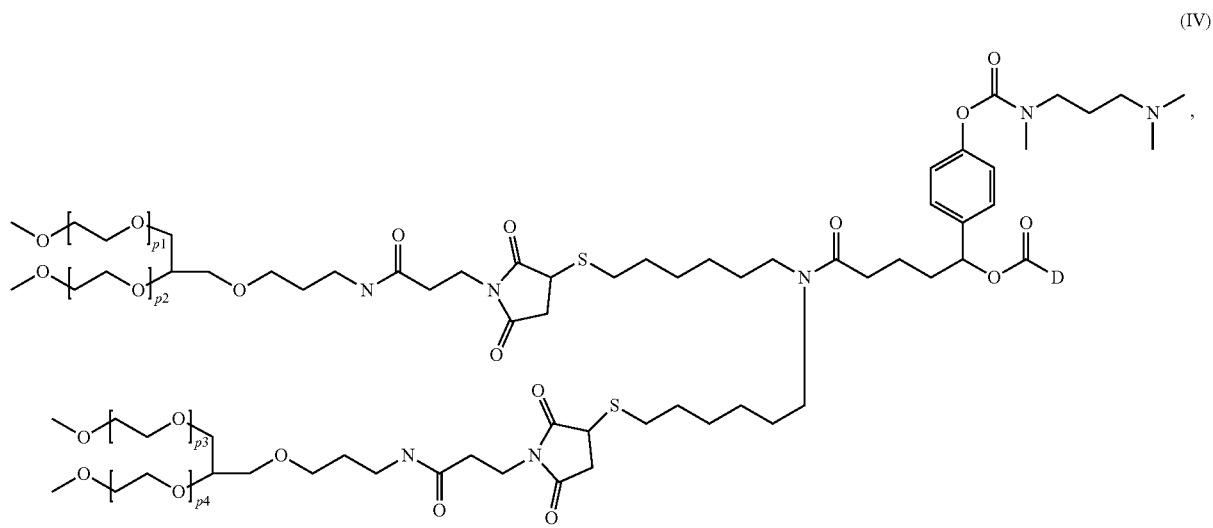

wherein
D is a hGH moiety connected to the rest of the molecule through an amine functional group; and
p1, p2, p3, p4 are independently an integer ranging from 170 to 284.

9. The method of claim 8, wherein p1, p2, p3, p4 are independently an integer ranging from 198 to 255.

10. The method of claim 9, wherein the hGH moiety is a polypeptide of SEQ ID NO:1.

11. The method of claim 10, wherein each administration of the long-acting growth hormone is at a dose of at least 0.16 mg/kg/week human growth hormone equivalents.

12. The method of claim 1, wherein the dose-of the long-acting growth hormone ranges from 0.24 mg/kg/week to 0.3 mg/kg/week human growth hormone equivalents.

* * * * *